United States Patent [19]
Akimoto et al.

[11] Patent Number: 5,849,716
[45] Date of Patent: Dec. 15, 1998

[54] SPHINGOGLYCOLIPIDS, THEIR PREPARATION, AND THERAPEUTIC METHODS OF USE

[75] Inventors: Koji Akimoto; Yasuhiko Koezuka, both of Takasaki, Japan

[73] Assignee: Kirin Beer Kabushiki Kaisha, Tokyo-to, Japan

[21] Appl. No.: 416,917

[22] PCT Filed: Oct. 22, 1993

[86] PCT No.: PCT/JP93/01523

§ 371 Date: Apr. 21, 1995

§ 102(e) Date: Apr. 21, 1995

[87] PCT Pub. No.: WO94/09020

PCT Pub. Date: Apr. 28, 1994

[30] Foreign Application Priority Data

Oct. 22, 1992 [JP] Japan .................................. 4-308124

[51] Int. Cl.⁶ ............................. A61K 31/70; C07H 15/00
[52] U.S. Cl. ........................... 514/25; 536/4.1; 536/17.9; 536/18.7; 536/18.5; 536/18.6; 536/53; 536/124; 424/520
[58] Field of Search .................... 536/4.1, 17.9, 536/18.7, 53, 18.5, 18.6, 124; 514/25; 424/520

[56] References Cited

U.S. PATENT DOCUMENTS

| | | | |
|---|---|---|---|
| 4,598,051 | 7/1986 | Papahad | 436/512 |
| 4,728,641 | 3/1988 | Iubaro | 514/54 |
| 4,806,466 | 2/1989 | Papahad | 435/7 |
| 4,816,450 | 3/1989 | Bell | 514/25 |
| 4,831,021 | 5/1989 | Tubaro | 514/54 |
| 4,859,769 | 8/1989 | Karlsson | 536/53 |
| 4,937,232 | 6/1990 | Bell | 514/26 |
| 4,952,683 | 8/1990 | Tschannen | 536/186 |
| 5,026,557 | 6/1991 | Estis | 424/450 |
| 5,028,715 | 7/1991 | Lyle | 548/193 |
| 5,041,441 | 8/1991 | Radin | 514/237.8 |
| 5,073,543 | 12/1991 | Marshall | 514/21 |
| 5,210,073 | 5/1993 | Yodoi | 514/12 |
| 5,567,684 | 10/1996 | Ladisch | 514/25 |

FOREIGN PATENT DOCUMENTS

| | | |
|---|---|---|
| 0254105 | 1/1988 | European Pat. Off. . |
| 371414 | 6/1990 | European Pat. Off. . |
| 0609437 | 8/1994 | European Pat. Off. . |
| 650732 | 5/1995 | European Pat. Off. . |
| 61-57594 | 3/1986 | Japan . |
| 62-39597 | of 1987 | Japan . |
| 63-45293 | 2/1988 | Japan . |
| 64-95 | of 1989 | Japan . |
| 1-93562 | 4/1989 | Japan . |
| 9356289 | 4/1989 | Japan . |
| 5-9193 | 1/1993 | Japan . |
| 5-59081 | 3/1993 | Japan . |
| 2588729 | 12/1996 | Japan . |
| 92-12986 | of 1992 | WIPO . |
| 9305055 | 3/1993 | WIPO . |

OTHER PUBLICATIONS

English translation of JP application 93562/1989 (Apr. 12, 1989).
English translation of claims of Japanese patent 2588729 (Dec. 5, 1996).
Hirsch, S., et al., "New Glycosphingolipids From Marine Organisms.", Tetrahedron, vol. 45, No. 12, (1989), pp. 3897–3906.
Sherida, W.P., et al. The Lancet, Oct. 14, 1989, pp. 891–895.
Brandt, S.J. The New England Journal of Medicine, vol. 318, Apr. 7, 1988, pp. 869–876.
Nienhuis, A.W. The Journal of Clinical Investigation. vol. 8, Aug. 1987, pp. 573–577.
Monroy, R.L. Blood. vol. 70, No. 5, Nov. 1987, pp. 1696–1699.
K.Munesada, et al. Chem. Soc. Perkin Trans. 1991 pp. 189–194.
R.J. Robb, The Journal of Immunology, vol. 136, 971–976 (1986).
Ende, N. "Life Sciences" vol. 51, pp. 1249–1253, 1992.
Motoki, K. "Radioprotective Effects . . . " Bioorganic and Medicinal Chemistry Letters, vol. 5, No. 22, pp. 2413–2416, 1995.
Uchida, et al; J. Biochem. 87:1843–1849 (1980).

(List continued on next page.)

Primary Examiner—Kathleen K. Fonda
Attorney, Agent, or Firm—Ladas & Parry

[57] ABSTRACT

The present invention relates to a sphingoglycolipid represented by the following formula (I) which is effective at a small dose and has an anti-tumor activity and an immuno-stimulating effect with few side-effects:

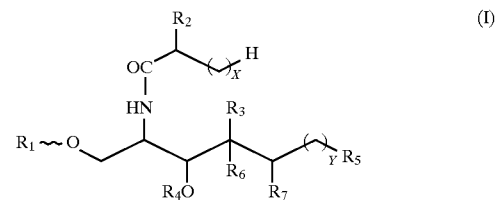

wherein

X denotes an integer from 10 to 24, Y denotes an integer from 9 to 13, $R_1$ represents a hexosyl, pentosyl, deoxyhexosyl, aminohexosyl, N-acetylaminohexosyl or a halide thereof or a sialic acid, $R_2$ represents H or a group $OR_2'$, wherein $R_2'$ represents H or a galactosyl or glucosyl group, $R_3$ represents H or a group $OR_3'$, wherein $R_3'$ represents H or a galactosyl or glucosyl group, $R_4$ represents a galactosyl group or H, $R_5$ represents a methyl or isopropyl group, $R_6$ and $R_7$ respectively represents H or form a double bond between the two carbon atoms to which $R_6$ and $R_7$ are attached, except for the case where $R_1$ represents α-galactosyl and $R_4$ represents H.

6 Claims, 7 Drawing Sheets

OTHER PUBLICATIONS

Inokuchi, et al. Cancer Letters, 38:23–30 (1987).

Higuchi, R., et al. "Structure and Biological Activity of Ganglioside Molecular Species." Liebigs Annalen der Chemie, vol. 1993, No. 4, Apr. 1993, pp. 359–366.

Hall, Eric. J. "Radiobiology for the Radiologist" Second Ed., Ch. 1, 9 and 11, 1978, Harper & Row Philadelphia.

Carroll, F.I., et al. J. Med. Chem., 1990, 33:2501–2508.

Komori, T. et al. Mass Spectrometry Rev. 1985, 4, 255–293.

Kalechman, Y., et al. The Journal of Immunology. Y. vol. 145, 1512–1517, Sep. 1, 1990.

E.G. Bremer, The Journal of Biological Chemstry, 261, 2434–2440 (1986).

Sugiyama, S., et al. "Biologically Active Glycosides . . . " Leibigs Annalen der Chemie; 1991, No. 4, pp. 349–356; (Apr. 4, 1991).

Schmidt, R.R., et al. "Synthesis of D–ribo–and L–lyxo–Phytosphingosi" Carbohydrate Research; vo. 174, (1988) pp. 169–179.

Radin, et al. Biochemical Pharmacology 37(15):2879–2886 (1988).

Kalisiak, et al. Int. J. Cancer 49:837–845 (1991).

Wiegand, et al. Chemical Abstracts 114:122965m (1991).

Shiio, T. Jpn J. Cancer Chemother. 15(3) Mar. 1988, pp. 481–485.

Taguchi, T. Jpn. J. Cancer Chemother. 12(2) Feb. 1985, pp. 366–378.

Kodo, H. et al. The Lancet. Jul. 2, 1988, pp. 38–39.

Blazar, B., et al. Blood, vol. 74, No. 6, Nov. 1, 1989, pp. 2264–2269.

Tamura, M. et al. Transplantation (Jun. 1991) vol. 51, No. 6, pp. 1166–1170.

Atkinson, K. et al. Blood, vol. 77, No. 6, Mar. 15, 1991, pp. 1376–1382.

Tanikawa, S. et al. Blood vol. 76, No. 3, Aug. 1, 1990, pp. 445–449.

Okano, A. et al. Transplantation, (1989) vol. 47, No. 4, pp. 738–740.

Isobe, R., et al. "Biomedical and Environmental Mass Spectrometry" vol. 13, 585–594 (1986).

Tsunematsu, H. et al. Biochemical and Biophysical Research Commnications, vol. 146, No. 2, 907–911 (1987).

Teshima, H. Exp. Hematol. vol. 17, 1989, pp. 853–858.

Souza, L.M., et al., Science, vol. 232, pp. 61–65 Apr. 4, 1986.

Zubay, G. "Biochemistry" pp. 527–535 Benjamin/Cummings Publlishing Co., Inc. 1983.

J. Chem. Soc. Perkin Transaction I, 1991, 1, 189–194.

Dillman, R.O. "Phase I . . . " Mol. Biother., 1992, vol. 4, 117–121.

Biokhimiya 49(3) 1984 pp. 432–436 Including English Abstract.

Sato, K. et al. "High Performance Tandem . . . " Anal. Chem. 1987, 59, 1652–1659.

Kawano, Y, et al. "Isolation and Structure . . . " Liebigs Ann Chem. 1988 19–24.

Higuchi, R. et al. "Structures of Three New Cerebrosides . . . " Liebigs Ann. Chem. 1990, 659–663.

Honda, M. et al. "Synthesis of a New . . . " Chem. Pharm. Bull. 39(6) 1385–1391 (1991).

Liguchi, R. et al. "Isolation and Characterization . . . " Liebigs. Ann. Chem 1990, 51–55.

Singh, B.N. et al. "Tegument Salactosylceramides . . . " Molecular and Biochemical Parasitology, 26. (1987) 99–112.

Hannun, Y.A. "Functions of Sphinsolipids . . . " Science, vol. 24–3. pp. 500–507.

Carbohydrate Research, vol. 162, No. 2, pp. 237–246 May 1, 1987 Koike, et al.

ALS Symposium Series: Gel Surface Glycolipide, vol. 128, pp. 35–54, 1980 Costello et al.

SPHINGOGLYCOLIPIDS, THEIR PREPARATION, AND THERAPEUTIC METHODS OF USE

This application is the U.S. national stage entry under 35 U.S.C. 371 of PCT/JP93/01523, filed Oct. 22, 1993.

TECHNICAL FIELD

The present invention relates to a novel sphingoglycolipid which is useful as an anti-tumor agent and an immunostimulating agent in the field of medicine.

BACKGROUND ART

The sphingoglycolipid is a complex glycolipid comprising as a lipid component a ceramide which is formed by an amide bond of a fatty acid with a long chain base, a monosaccharide or an oligosaccharide being bonded to the primary alcohol of the ceramide via glycoside bond. The review of the sphigoglycolipid including the history of its discovery, the components of the complex glycolipid and its preparation methods has been described in SHIN-SEIKAGAKU JIKKEN KOZA NO. 4, LIPIDS III, GLYCOLIPIDS, 1990, TOKYO KAGAKU DOJIN.

A sphingoglycolipid which is recognized to have an anti-tumor or immunostimulating effects includes sphingoglycolipids which have been extracted and isolated from a poriferan, Agelas mauritianus, by the present inventors (Japanese Patent Laid-Open Publication Nos. 303314/1990, 244385/1991 and 244384/1991, and PCT/JP92/00561).

In addition to the sphingoglycolipids described above, there has been described only one sphingoglycolipid in Japanese Patent Laid-Open Publication No. 93562/1989 to the best of the knowledge of the present inventors. The sphingoglycolipid however must be administered at a very large amount of 0.5–2 mg/mouse, and thus has not been put to the practical use.

A variety of anti-tumor agents and immunostimulating agents have hitherto been developed, but none of these agents were satisfactory from the aspect of their effects or side-effects. The object of the present invention is to provide an anti-tumor and immunostimulating agent which is effective at a small dose and has little side-effect.

DISCLOSURE OF THE INVENTION

The present inventors have created a process for synthesizing an aldopyranosyl- or aldofuranosyl-sphingoglycolipid and found that the compound exhibits an anti-tumor activity and an immunostimulating effect. Thus, they have accomplished the present invention on the basis of this information.

That is, the compound according to the present invention is the sphingoglycolipid represented by the following formula (I):

(I)

wherein

X denotes an integer from 10 to 24, Y denotes an integer from 9 to 13, $R_1$ represents a hexosyl, pentosyl, deoxyhexosyl, aminohexosyl, N-acetylaminohexosyl or a halide thereof or a sialic acid, $R_2$ represents H or a group $OR_2'$, wherein $R_2'$ represents H or a galactosyl or glucosyl group, $R_3$ represents H or a group $OR_3'$, wherein $R_3'$ represents H or a galactosyl or glucosyl group, $R_4$ represents a galactosyl group or H, $R_5$ represents a methyl or isopropyl group, $R_6$ and $R_7$ respectively represents H or form a double bond between the two carbon atoms to which $R_6$ and $R_7$ are attached, except for the case where $R_1$ represents α-galactosyl and $R_4$ represents H, and the following compounds (i)–(viii):

(i) 1-(2-acetamino-2-deoxy-α-D-galactopyranosyloxy)-2-octadecanoylamino-3-octadecanol;

(ii) 1-(2-acetamino-2-deoxy-α-D-glucopyranosyloxy)-2-octadecanoylamino-3-octadecanol;

(iii) 1-[2-acetamino-2-deoxy-4-(β-D-galactopyranosyloxy)-α-D-galactopyranosyloxy]-2-octadecanoylamino-3-octadecanol;

(iv) 1-[2-acetamino-2-deoxy-4-(β-D-galactopyranosyloxy)-α-D-galactopyranosyloxy]-2-octadecanoylamino-4-octadecen-3-ol;

(v) (2S,3R,4E)-1-β-D-glucopyranosyloxy-2-hexadecanoylamino-4-eicosen-3-ol;

(vi) (2S,3R,4E)-1-β-D-glucopyranosyloxy-2-hexadecanoylamino-4-octadecen-3-ol;

(vii) (2S,3R,4E)-1-O-(sodium 5-acetamido-3,5-dideoxy-D-glycero-β-D-galacto-2-nonulopyranosylonate)-2-tetracosanamido-4-octadecene-1,3-diol; and (viii) (2S,3R,4E)-1-O-(sodium 5-acetamido-3,5-dideoxy-D-glycero-α-D-galacto-2-nonulopyranosylonate)-2-tetracosanamido-4-octadecene-1,3-diol.

The present invention also relates to the use of the compound.

That is to say, the anti-tumor agent and the immunostimulating agent according to the present invention contain the compound represented by the formula (I) as an effective ingredient.

BEST MODE FOR CARRYING OUT THE INVENTION

Sphingoglycolipid

Figure 1:
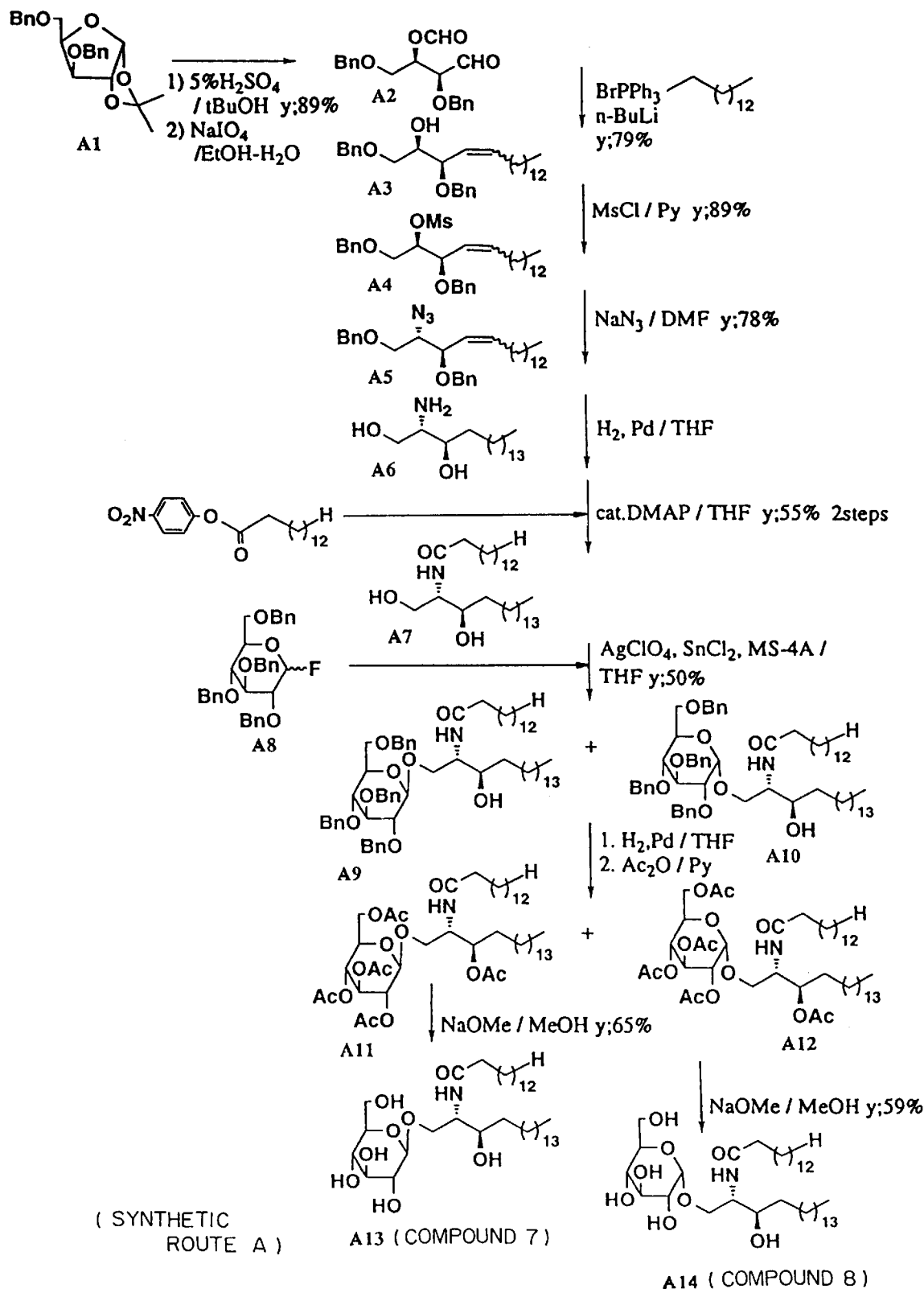
FIG. 1 shows a reaction scheme of the synthetic route A.

The sphingoglycolipid according to the present invention is, as described above, the compound represented by the formula (I) and has the structure formed by the glycosyl bond of a ceramide with a monosaccharide (aldopyranosyl or aldofuranosyl) or a derivative thereof. The derivative includes a deoxysaccharide in which one or two of the hydroxyl groups in the monosaccharide are deoxidized or a halogenosaccharide in which one or two of the hydroxyl groups are halogenized (with chlorine, fluorine, bromine or iodine) as well as an aminosaccharide such as galactosamine or glucosamine, an N-acetylaminosaccharide such as N-acetylgalactosamine or N-acetylglucosamine, and a sialic acid such as N-acetylneuraminic acid (NANA) or N-glycolylneuraminic acid.

In the monosaccharide of $R_1$, the hexosyl is selected from the group consisting of glucosyl, mannosyl, allosyl, altrosyl, gulosyl, idosyl, talosyl and galactosyl, the pentosyl is selected from the group consisting of xylosyl, arabinosyl, ribosyl and lyxosyl, the deoxyhexosyl is preferably selected from the group consisting of 2-deoxygalactosyl, 2-deoxyglucosyl, 6-deoxygalactosyl and 6-deoxyglucosyl, the aminohexosyl is preferably selected from the group consisting of galactosaminyl and glucosaminyl, and the N-acetylaminohexosyl is preferably selected from the group consisting of N-acetylgalactosaminyl and N-acetylglucosaminyl.

The monosaccharide and the derivative thereof may have the α-bond and the β-bond and exhibit an anti-tumor and immunostimulating effect in either of these bonds. While the compound of the formula (I) has a saturated chain between the 4- and 5-positions, a derivative of the compound with an unsaturated chain in which a double bond is inserted between these positions, i.e. a double bond is formed between the two carbon atoms to which $R_6$ and $R_7$ are respectively attached, also exhibits the similar effects. Furthermore, it is also possible in the compound of formula (II) to incorporate two saccharides in the ceramide by selectively protecting the two hydroxyl groups in the ceramide and thus introducing the different saccharides (galactosyl or glucosyl) into each of the hydroxyl groups.

Specific examples of the compounds of this invention represented by the formula (I) preferably include those listed below.

(1) Compounds represented by the following formula (II):

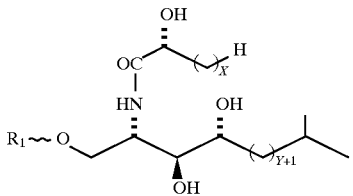
(II)

Compound 1 (2S,3S,4R)-1-(α-D-glucopyranosyloxy)-2-[(R)-2-hydroxytetracosanoylamino]-16-methyl-3,4-heptadecane-diol,
Compound 2 (2S,3S,4R)-1-(β-D-glucopyranosyloxy)-2-[(R)-2-hydroxytetracosanoylamino]-16-methyl-3,4-heptadecanediol,
Compound 3 (2S,3S,4R)-1-(β-D-galactopyranosyloxy)-2-[(R)-2-hydroxytetracosanoylamino]-16-methyl-3,4-heptadecanediol.

(2) Compounds represented by the following formula (III):

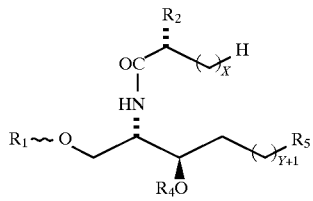
(III)

Compound 4 (2S,3R)-1,3-di-(α-D-galactopyranosyloxy)-2-[(R)-2-hydroxytetracosanoylamino]octadecane,
Compound 5 (2S,3R)-1-(α-D-galactopyranosyloxy)-3-(β-D-galactopyranosyloxy)-2-[(R)-2-hydroxytetracosanoylamino]octadecane,
Compound 6 (2S,3R)-1,3-di-(α-D-galactopyranosyloxy)-2-octadecanoylaminoheptadecane.

(3) Compounds represented by the following formula (IV):

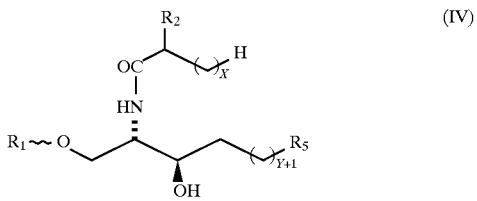
(IV)

Compound 7 (2S,3R)-1-(β-D-glucopyranosyloxy)-2-tetradecanoylamino-3-octadecanol,
Compound 8 (2S,3R)-1-(α-D-glucopyranosyloxy)-2-tetradecanoylamino-3-octadecanol,
Compound 9 (2S,3R)-1-(β-D-galactopyranosyloxy)-2-tetradecanoylamino-3-octadecanol,
Compound 10 (2S,3R)-1-(α-D-xylofuranosyloxy)-2-tetradecanoylamino-3-octadecanol,
Compound 11 (2S,3R)-1-(β-D-xylopyranosyloxy)-2-tetradecanoylamino-3-octadecanol,
Compound 12 (2S,3R)-1-(6'-deoxy-α-D-galactopyranosyloxy)-2-tetradecanoylamino-3-octadecanol,
Compound 13 (2S,3R)-1-(6'-deoxy-α-D-galactopyranosyloxy)-2-tetradecanoylamino-3-octadecanol,
Compound 14 (2S,3R)-1-(6'-deoxy-α-D-galactofuranosyloxy)-2-tetradecanoylamino-3-octadecanol,
Compound 15 (2S,3R)-1-(6'-deoxy-α-D-galactofuranosyloxy)-2-tetradecanoylamino-3-octadecanol,
Compound 16 (2S,3R)-1-(2'-deoxy-α-D-galactopyranosyloxy)-2-tetradecanoylamino-3-octadecanol,
Compound 17 (2S,3R)-1-(β-L-arabinopyranosyloxy)-2-tetradecanoylamino-3-octadecanol,
Compound 18 (2S,3R)-1-(α-L-arabinopyranosyloxy)-2-tetradecanoylamino-3-octadecanol.

(4) Compounds represented by the following formula (V):

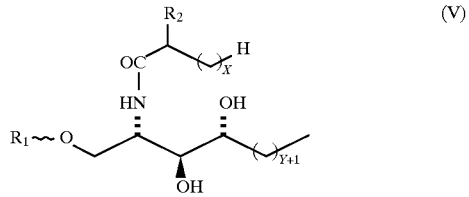
(V)

Compound 19 (2S,3S,4R)-1-(α-D-glucopyranosyloxy)-2-hexacosanoylamino-3,4-octadecanediol,
Compound 20 (2S,3S,4R)-1-(α-D-glucopyranosyloxy)-2-tetracosanoylamino-3,4-tridecanediol,
Compound 21 (2S,3S,4R)-1-(α-D-glucopyranosyloxy)-2-tetracosanoylamino-3,4-henicosanediol,
Compound 22 (2S,3S,4R)-1-(α-D-glucopyranosyloxy)-2-acetamino-3,4-undecanediol,
Compound 23 (2S,3S,4R)-1-(α-D-glucopyranosyloxy)-2-tetradecanoylamino-3,4-pentadecanediol,
Compound 24 (2S,3S,4R)-1-(α-D-glucopyranosyloxy)-2-octanoylamino-3,4-nonadecanediol,
Compound 25 (2S,3S,4R)-1-(α-D-glucopyranosyloxy)-2-eicosanoylamino-3,4-heptadecanediol,
Compound 26 (2S,3S,4R)-1-(α-D-glucopyranosyloxy)-2-[(R)-2-hydroxyhexacosanoylamino]-3,4-henicosanediol, Compound 27 (2S,3S,4R)-1-(α-D-glucopyranosyloxy)-2-[(R)-2-hydroxyoctadecanoylamino]-3,4-heptadecanediol,
Compound 28 (2S,3S,4R)-1-(α-D-glucopyranosyloxy)-2-[(R)-2-hydroxyoctanoylamino]-3,4-tridecanediol,
Compound 29 (2S,3S,4R)-1-(α-D-glucopyranosyloxy)-2-[(R)-2-hydroxytetracosanoylamino]-3,4-nonadecanediol,
Compound 30 (2S,3S,4R)-1-(α-D-glucopyranosyloxy)-2-[(S)-2-hydroxytetracosanoylamino]-3,4-nonadecanediol.

Among these compounds, the compounds 1, 4, 6, 8, 10, 12, 16, 17 and 19–30 are more preferred, and the compounds 8, 12, 16, 17 and 19–30 are particularly preferred.

Process for preparing the compound of the present invention

While some of the compounds according to the present invention, that is the sphingoglycolipids represented by the formula (I), can be derivatized from sphingosine by various chemical modifications, it is also possible to prepare the sphingoglycolipid by the total synthesis with chemical synthetic means which comprise the various general chemical reactions required for synthesizing the sphingoglycolipid. The route of the total synthesis of sphingoglycolipid is not limited to only one route, but the compound can be prepared by a variety of routes starting from different materials. As an example of the general means of the chemical synthesis for the sphingoglycolipid, it is also possible to synthesize it with accordance to the method described in Agricultural and Biological chemistry, 54 (3), 663, 1990. As an example of using a variety of saccharides as the starting material, it is also possible to prepare the sphingoglycolipid with accordance to the method described in Liebigs Annalen der Chemie, 663, 1988. These synthetic methods in principle comprise combining the ceramide with a saccharide before removing the protecting groups of the ceramide, but it is also possible first to bond a saccharide to the long chain and then to derivatize the amino group into the amide group to complete the cerebroside.

(Synthetic Route A)

As an example of such synthesis, it is also possible to synthesize the compound represented by the formula (I) via the following steps (see FIG. 1). In FIG. 1, the following abbreviations are used.
Bn: benzyl,
Ms: methanesulfonyl,
DMAP: 4-dimethylaminopyridine,
MS-4A: Molecular Sieves-4A (dehydrating agent),
Ac: acetyl.

The aldehyde A2 as a raw material has a few asymmetric carbons. An amino acid or a saccharide may be also used as the sources of these asymmetries. The four diastereoisomers of 2-amino-1,3-alkanediol A6, obtained by the reduction of A2, can be prepared as an individual isomer by appropriately selecting the asymmetry sources of the original aldehyde, and these isomers are separately subjected to amidation. The route shown in the scheme represents one of these routes. In this route, while a benzyl group is employed as the protecting group of the hydroxyl group, any other appropriate groups such as a isopropylidene group may also be used.

In this route scheme, many methods of reaction are known particularly for the amidation. It is also possible to use an acid chloride, an acid anhydride or a carboxylic acid per se in place of the active carboxylate.

The reaction with carboxylic acid is a condensation reaction in the presence of an appropriate condensing agent. The appropriate condensing agent used in the reaction includes dicyclohexylcarbodiimide (DCC), 2-ethoxy-1-ethoxycarbonyl-1,2-dihydroquinoline (EEDQ), 1-ethyl-3-(3'-dimethylaminopropyl)carbodiimide (WSC), a chlorocarbonic ester and an onium salt. In order to progress rapidly the reaction, an organic base such as triethylamine, pyridine, N-methylmorpholine, dimethylaniline, 4-dimethylaminopyridine, N-methylpiperidine, N-methylpyrrolidine is added. The solvent may be any one of inert solvents which will not be involved in the reaction such as tetrahydrofuran, ethyl ether, benzene, toluene, chloroform, methylene chloride, ethyl acetate, acetone or the like.

The reaction with an acid chloride generally proceeds conveniently in the presence of the solvent. The reaction is generally carried out with an appropriate solvent, but when the reaction rate is low, it can be increased by performing the reaction in the absence of a solvent. The solvent may be any one of inert solvents which will not be involved in the reaction, e.g. those described above. When the reaction proceeds slowly, it may proceed rapidly on the addition of an organic base such as triethylamine, pyridine, N-methylmorpholine, dimethylaniline or 4-dimethylaminopyridine.

The reaction with the acid anhydride is preferably carried out in the presence of an appropriate base. The base used in the reaction includes triethylamine or pyridine, which is usually used also as a solvent.

Further, many reactions for glycosylation are known and for example described in the following reviews: 1) YUKI GOSEI KAGAKU, Vol. 38, No. 5, page 473, 1980; 2) YUKI GOSEI KAGAKU, Vol. 41, No. 8, page 701, 1983; 3) Pure and Applied Chemistry, Vol. 61, No. 7, page 1257, 1989; 4) Pharmacia, Vol. 27, No. 1, page 50, 1991; 5) JIKKEN KAGAKU KOZA, 4th version, Vol. 26, page 267, MARUZEN. Glycosylation is successfully carried out via any of the reactions described in those reviews. If it is difficult to separate the α-glycoside and the β-glycoside, the two isomers may be easily separated by converting the hydroxyl group into the acyl derivative such as the acetyl derivative.

(Synthetic Route B)

Figure 2:
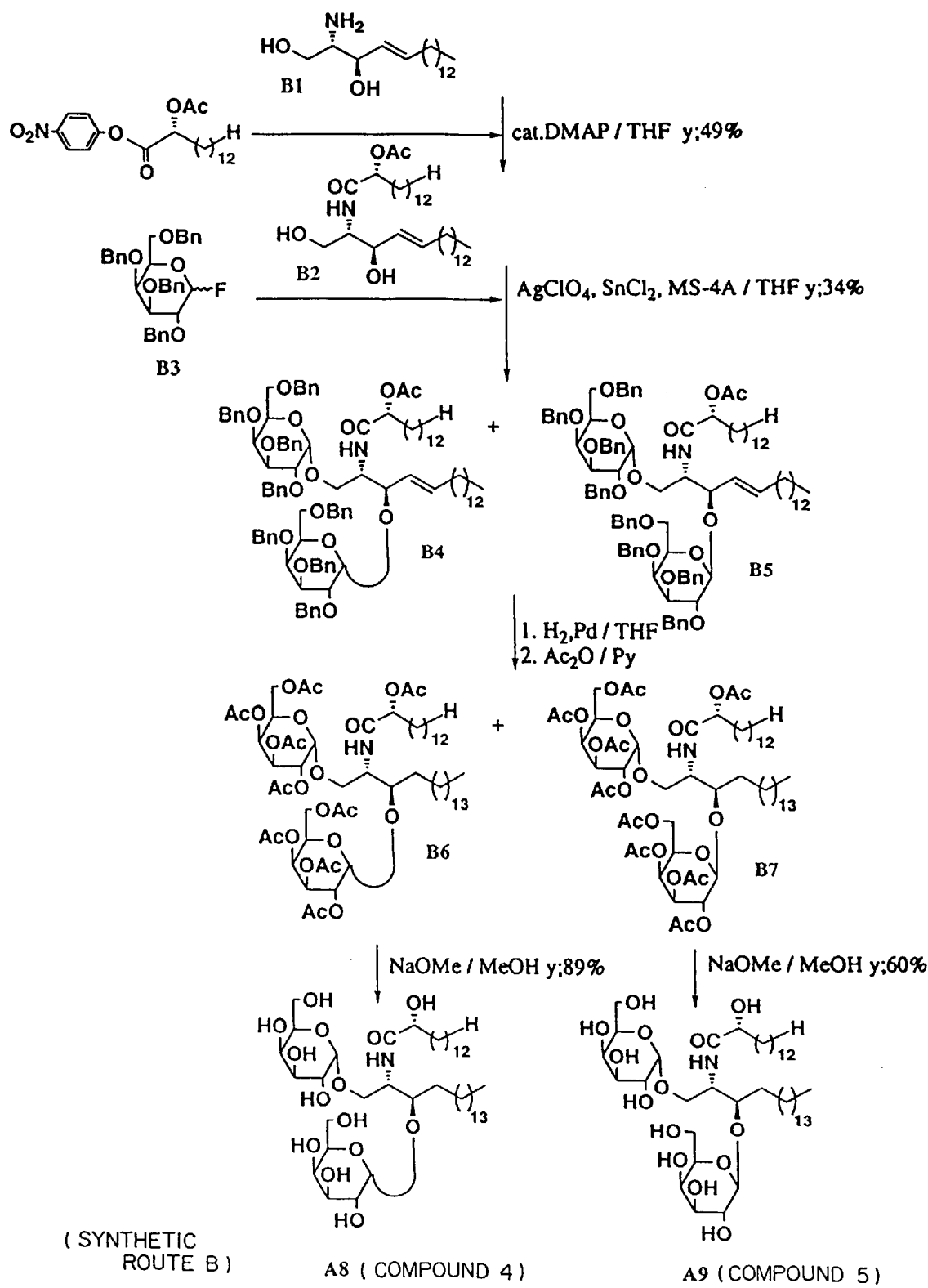
FIG. 2 shows a reaction scheme of the synthetic route B.

As an example of the synthesis of the compound of the formula (I) carried out by making a variety of chemical modifications of sphingosine, it is also possible to prepare the compound of the formula (I) in which the long chain base part has 18 carbon atoms via the following steps (see FIG. 2). In FIG. 2, the same abbreviations as above are used. While the sphingosine can be prepared by the extraction from natural sources, it is also commercially available from Sigma Chemical Company or FUNAKOSHI K.K. It is also possible to synthesize the sphingosine by a variety of synthetic methods as described in Pharmacia, Vol. 27, page 1164, 1991 or Journal of the Chemical Society, Perkin Transactions 1, 2279, 1991. The isomeric sphingosines having a configuration different from that of the natural sphingosine can also be prepared according to the methods described in Helvetica Chimica Acta, 40, 1145, 1957 or Journal of the Chemical Society, Chemical Communications, 820, 1991. Furthermore, many examples of synthesis are described in the latter reference. In this route, it is possible to keep the double bond in the molecule even after glycosylation. That is to say, a compound having no double bond is obtained by catalytic reduction in the final deprotection step, and a compound having a double bond is prepared by the reaction of metal sodium in liquid ammonia, so that it is possible to prepare separately each of the compounds.

(Synthetic Route C)

Figure 3A:
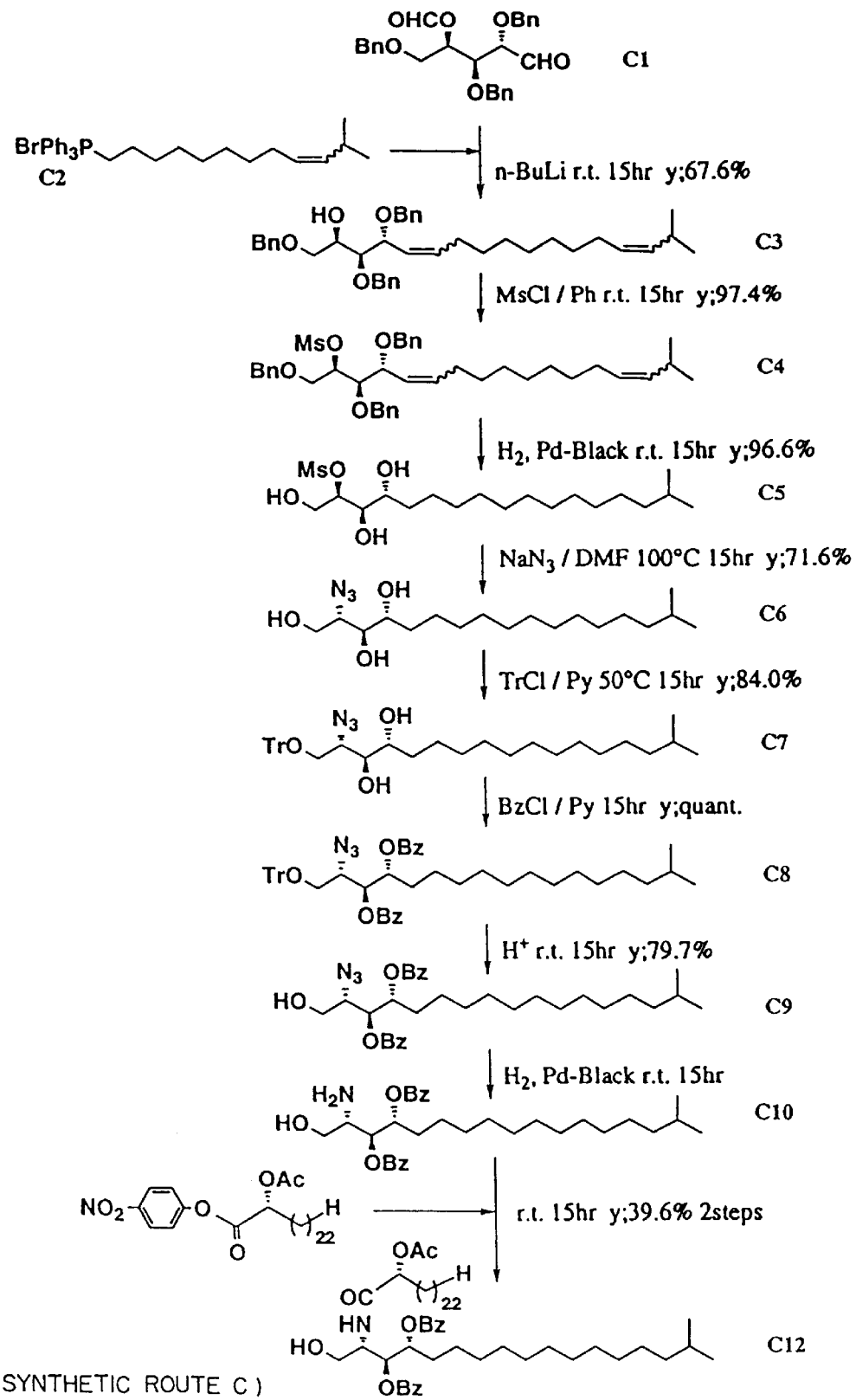
FIGS. 3(a) and (b) show a reaction scheme of the synthetic route C.
Figure 3B:
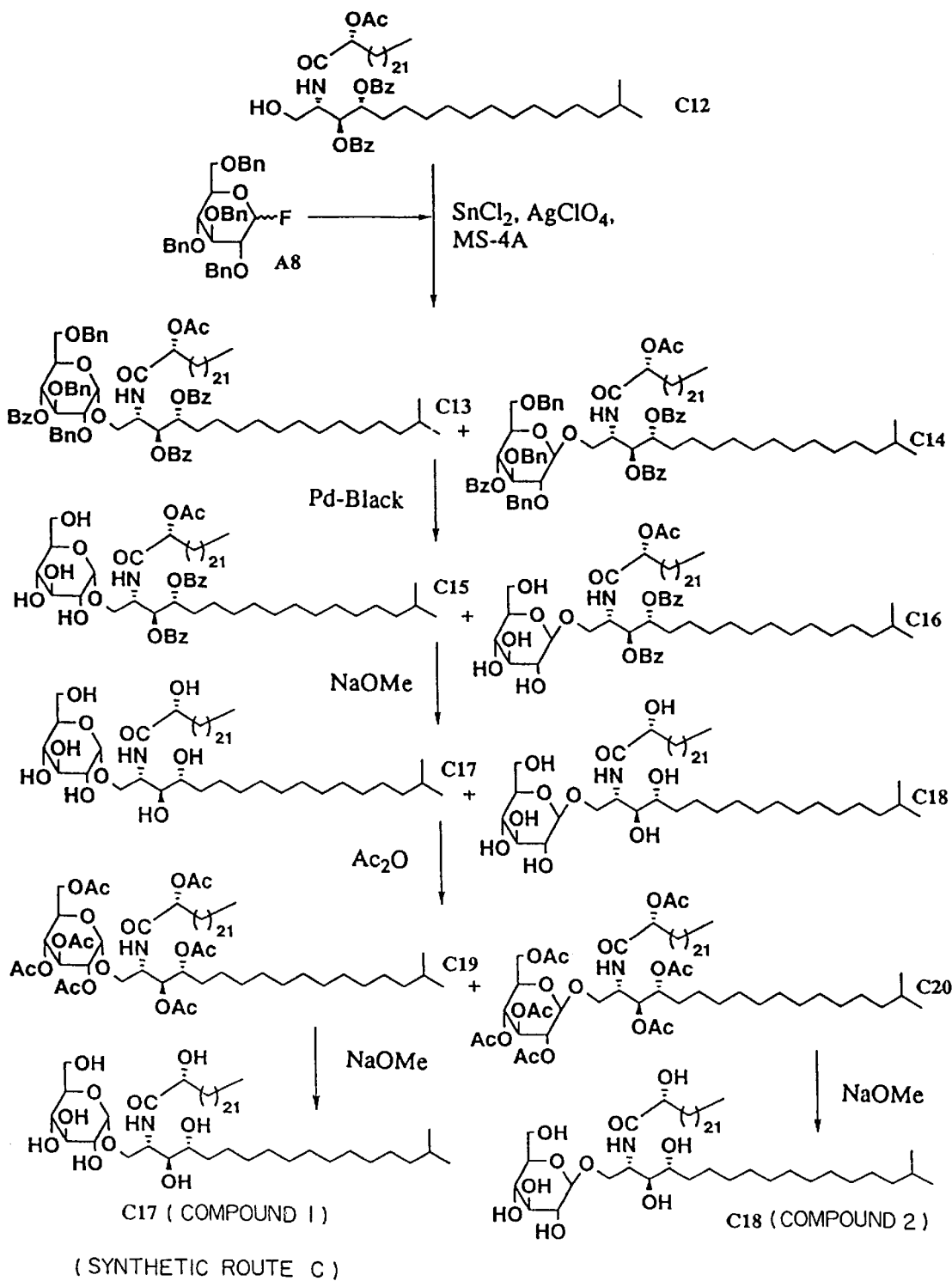

Furthermore, the compound having a hydroxyl group at the 4-position such as those represented by the formulae (II) and (V) can also be synthesized via the following steps (see FIG. 3(a) and (b)). In FIG. 3, the same abbreviations as above are used.

The aldehyde C1 as a starting material can be prepared as an individual isomer by appropriately selecting the asymmetry sources of the raw material. These isomers are individually subjected to the next Wittig reaction. The terminals of these Wittig salts can be easily made into iso-, ante-iso- or straight chain forms. In general, the Wittig reaction with use of such labile ylides gives a cis-type double bond as a main product with a little contamination of a trans-type double bond. Such a mixture will offer no problem, since these double bonds are equally converted into a single bond during the step of catalytic reduction. The intermediate is subjected to mesylation, azide inversion, protection of the hydroxyl groups and reduction to form an amino derivative, which is further subjected to amidation to form a ceramide. The ceramide with a protecting group as an intermediate is also obtained by attaching an appropriate protecting group such as acetyl, benzoyl or benzyl groups to a commercially available CEBRINE E (Alfred Bader Chemicals or K & K Laboratories, Inc.) as a raw material. The aimed compound can be obtained by glycosylation and deprotection (see FIGS. 3(a) and (b)).

(Synthetic Route D)

Figure 4:
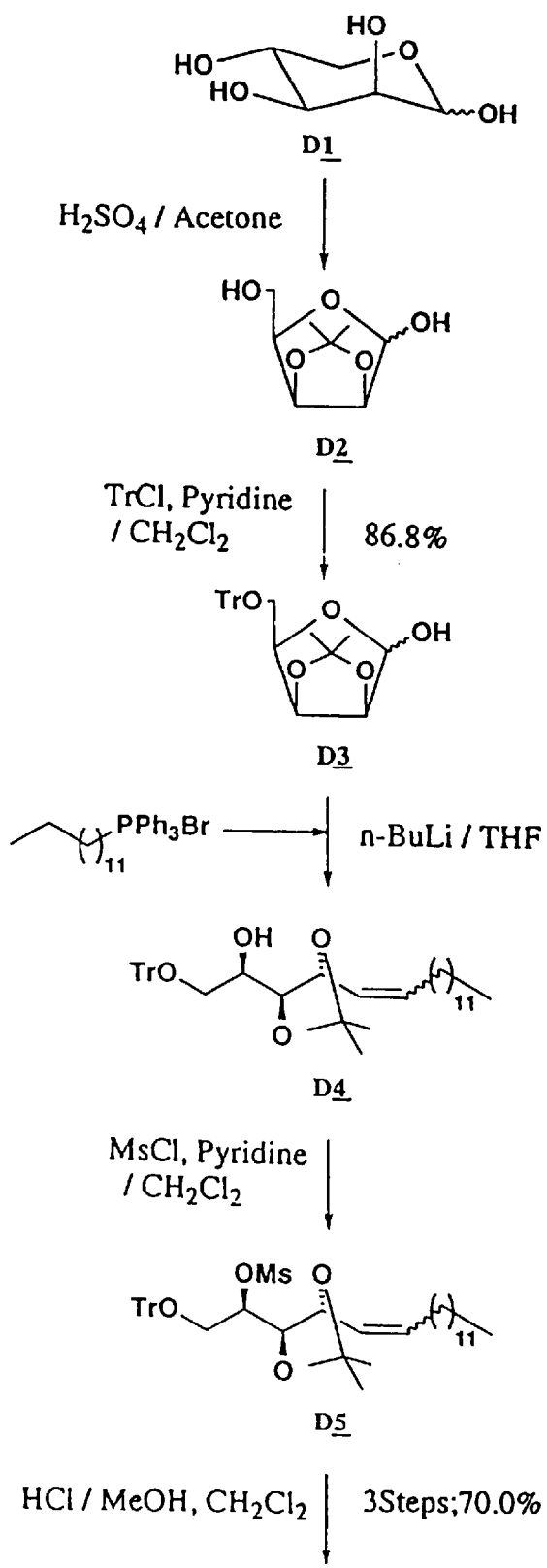
FIGS. 4(a), (b) and (c) show a reaction scheme of the synthetic route D.
Figure 4B:
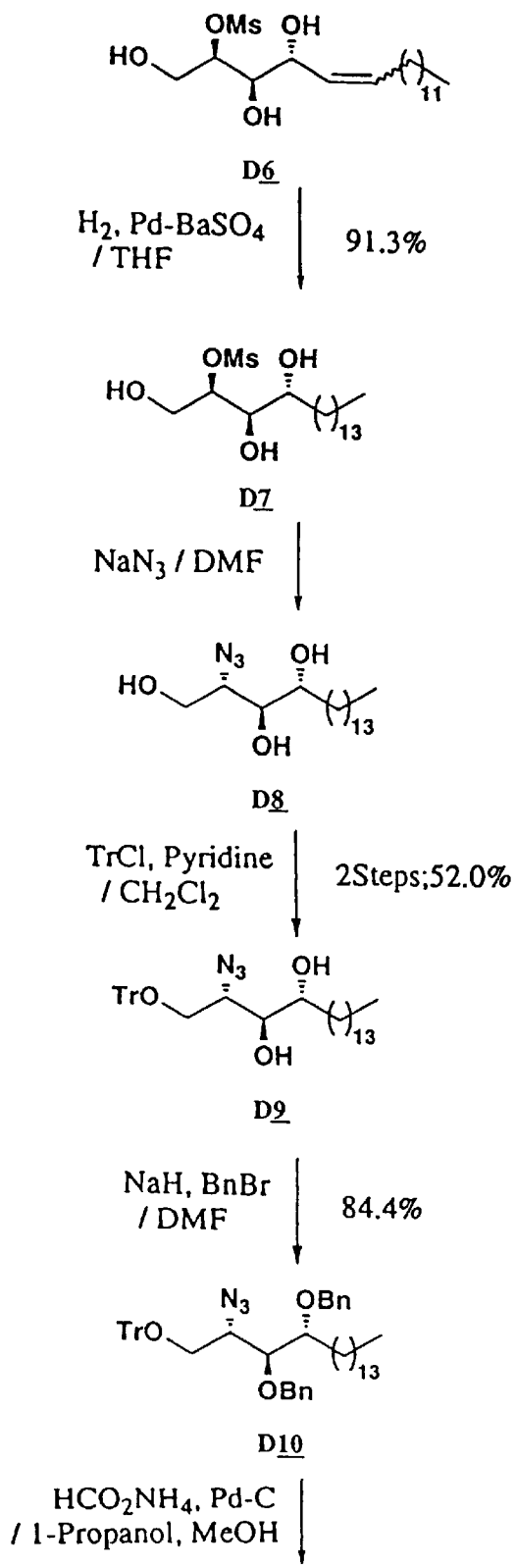
Figure 4:
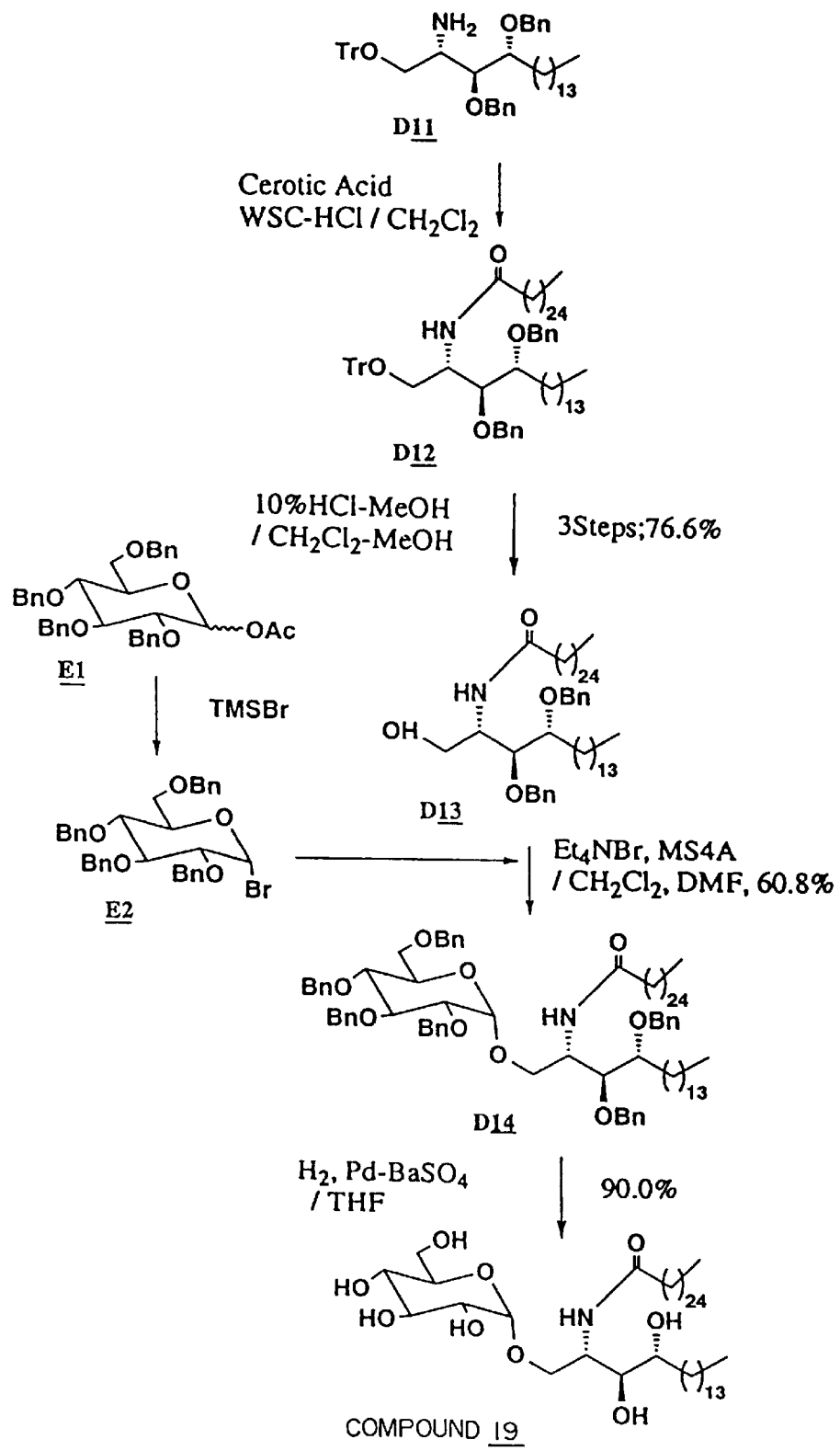

The compound having a hydroxyl group at the 4-position of the long chain base can also be synthesized via the following steps in the same manner as in Synthetic Route C (see FIGS. 4(a)–(c)). In the figures, the same abbreviations as above are used.

This route is characterized by the use of a commercially available D-lyxose as a starting material. The lyxose of which 2- and 3-positions are protected with an acetonide and 5-position with a trityl group, is subjected to Wittig reaction in the same manner as in Synthetic Route C, followed by mesylation, deprotection, catalytic reduction, azide inversion, introduction of a protecting group and reduction to form an amino derivative, which is further subjected to amidation to give a ceramide. The aimed compound can be obtained by selective deprotection followed by glycosylation and deprotection.

Uses of the compound of the present invention

The compounds represented by the formulae (I) or (II)–(V) exhibit the following physiological activities, i.e. anti-tumor activity and immunostimulating effect, and can be used as an immunotherapeutic agent against cancers (an anti-tumor agent) or as an immunostimulating agent against the other diseases.

1) Anti-tumor activity

The compound of the present invention exhibited an anti-tumor activity against B16 mouse melanoma cells inoculated subcutaneously in mice as shown in Experimental Example 1 described below.

2) Immunostimulating activity

The compound of the present invention exhibited an MLR propagating activity in the test of the mixed lymphocyte culture reaction (MLR) in mice as shown in Experimental Example 2 described below.

3) Anti-tumor agent and immunostimulating agent

As mentioned above, the compound of the present invention has an anti-tumor activity and an immunostimulating effect and thus can be used as an anti-tumor agent (immunotherapeutic agent against carcinoma).

While the immunotherapeutic agent against carcinoma may be used alone, it is also used in combination with chemotherapy or radiotherapy. Such uses are reviewed in Pharmaceutical Society of Japan, Pharmacia Review, Vol. 23, Chemistry for Conquering Cancer, Continuation, page 105, 1987; Medical View Co., Ltd., Illustration of Clinical "Cancer" Series No. 19, Carcinoma and Immune, page 159, 1987; and IGAKU NO AYUMI (Progress of Medical Science), Vol. 150, NO. 14, page 1018, 1989.

The compound of the present invention as an anti-tumor agent or an immunostimulating agent may be administered in any appropriate dosage route and in a dosage form determined by the dosage route adoped. The compound is generally formed into a preparation which is in the form diluted and formed with a pharmaceutically acceptable additive (carrier or diluent). When the compound of the present invention is used as an anti-tumor agent or an immunostimulating agent, it can be administered orally or parenterally to human or mammalian. For example, the compound of the present invention can be administered intravenously, intramuscularly or subcutaneously in a form for injection such as solution, suspension or emulsion with an appropriate solvent for injection (for example, distilled water for injection). In this case, polysorbates or macrogols can also be added as a solubilizing agent, if necessary. Alternatively, the compound may be orally administered in a form such as powder, a tablet, granule, a capsule, a troche or dry syrup into which an appropriate additive, e.g. any conventional compounds used for this object such as starch, lactose, crystalline cellulose, hydroxypropylcellulose (HPC), carboxymethylcellulose calcium (CMC-Ca) or magnesium stearate is incorporated.

The dose of the compound of the present invention is determined so that the total dose does not to exceed a certain level upon continuous or intermittent administration of it in consideration of the results of animal tests as well as individual conditions. Specific dose varies depending on its dosage forms and routes, the conditions of human or animal such as age, body weight, sex, sensitivity, feed, dosage period, drugs used in combination, or seriousness of patients or the disease, and the optimum dose and the dosage times under the certain condition must be determined by the test for determining an optimum dose by the medical specialist on the basis of the aforementioned guideline. In this connection, the mimimal dose required for the expressing the activity of the compound of the present invention is generally in the range of about 0.001 mg/kg body weight of the host.

EXAMPLE

[EXPERIMENTAL EXAMPLES]

The present invention is further described below in detail with reference to experimental examples without limit thereto.

Example 1

Synthesis of the compound of the present invention

The synthetic method and phsicochemical properties of the compound of the present invention are described below (referring to the number of compounds in the process of synthesis, see the reaction schemes shown in FIGS. 1–4).

(1) Synthetic Route A

The route shows specifically the process for preparing the compounds 7 and 8, and the compounds according to the present invention 4–6, and 9–18 can also be synthesized in accordance with this process (see FIG. 1).

In the schemes shown above, the following abbreviations are used:

DMAP: 4-dimethylaminopyridine;

TsOH: p-toluenesulfonic acid;

MS-4A: Molecular Sieves-4A (dehydrating agent).

The other abbreviations has the same meanings as those in the schemes shown above.

(Synthesis of compounds 7 and 8 (FIG. 1))

Compound A1 may be prepared according to the method described in Synthesis, 961–963, 1984.

(i) Synthesis of Compound A2

To a solution of 2.89 g of Compound A1 in 25 ml of 2-methyl-2-propanol was added 25 ml of a 5% aqueous sulfuric acid solution. The mixture was stirred at 45° C. for 15 hours. Powdery sodium hydrogen carbonate was added under ice-cooling to neutralize the reaction mixture, which was then concentrated. A 30 ml of water was added to the residue, which was extracted thrice with ethyl acetate and concentrated. Purification on a silica gel column (Wako Gel C-200, 100 g, hexane:acetone=2:1) gave a diol in an amount of 2.28 g (yield 88.5%).

MS: FDMS 330.

To 2.25 g of the diol were added 50 ml of ethanol, 12 ml of water, and 2.33 g of sodium metaperiodate and the mixture was stirred at room temperature for 10 hours. Deposits were removed by filtration, and the filtrate was concentrated. Chloroform was added to the residue, which was washed with brine, concentrated to give an aldehyde (Compound A2) in an amount of 1.31 g. The product was used for the next reaction without further purification.

(ii) Synthesis of Compound A3

To 213.7 g of tetradecanetriphenylphosphonium bromide was added 630 ml of tetrahydrofuran, and the reactor was purged with argon gas. A 173 ml of a 2.3N n-butyl lithium—hexane solution was added at −30° C., and the mixture was stirred for 3.5 hours. A solution of 31.73 g of the (2R,3R)-aldehyde (Compound A2) in 630 ml of tetrahydrofuran was added dropwise, and the mixture was stirred for 2 hours, concentrated, diluted with ethyl acetate, washed with water and brine, and concentrated. Purification on a silica gel column (Wako Gel C-200, 850 g, hexane:ethyl acetate=9:1) gave an alcohol (Compound A3) in an amount of 36.31 g (yield 79.0%).

MS: FDMS 481.

NMR: $^1$H (500 MHz, CDCl$_3$; 27° C.) δ(ppm) 7.26–7.46 (10H, m), 5.69–5.78 (1H, m), 5.31–5.38 (1H, m), 4.34–4.63 (5H, m), 4.28 (0.7H, dd, J=6.7, 9.2 Hz), 3.85 (0.3H, t, J=7.3 Hz), 3.75–3.78 (1H, m), 3.56–3.60 (1H, m), 3.47 (1H, dd, J=5.5, 10.4 Hz), 1.98–2.11 (2H, m), 1.26–1.34 (22H, m), 0.88 (3H, t, J=6.7 Hz).

(iii) Synthesis of Compound A4

To 5.03 g of the alcohol (Compound A3) were added 50 ml of pyridine followed by 1.62 ml of methanesulfonyl chloride, and the mixture was stirred at room temperature for 16 hours, concentrated and azeotropically distilled together with toluene. The residue was diluted with diethyl ether and washed with brine, concentrated and purified on a silica gel column (Wako Gel C-200, 200 g, hexane:acetone=10:1) gave an mesyl derivative (Compound A4) in an amount of 5.20 g (yield 88.9%).

MS: FDMS 558.

NMR: $^1$H (500 MHz, CDCl$_3$; 27° C.) δ(ppm) 7.23–7.35 (10H, m), 5.77–5.83 (1H, m), 5.26–5.35 (1H, m), 4.71–4.77 (1H, m), 4.33–4.62 (5H, m), 4.06 (0.3H, t, J=8.1 Hz), 3.74 (0.7H, dd, J=3.1, 11.0 Hz), 3.65–3.70 (1H, m), 2.964 (0.9H, s), 2.956 (2.1H, s), 1.99–2.17 (2H, m), 1.26–1.37 (22H, m), 0.88 (3H, t, J=6.8 Hz).

(iv) Synthesis of Compound A5

To 1.52 g of the mesyl derivative (Compound A4) were added 20 ml of dimethylformamide and 1.42 g of sodium azide, and the mixture was stirred at 120° C. for 12 hours. Brine was then added to the mixture, which was extracted thrice with ethyl acetate, concentrated and purified on a silica gel column (Wako Gel C-200, 50 g, hexane:ethyl acetate=40:1) to give an azide (Compound A5) in an amount of 1.07 g (yield 77.7%).

IR: (cm$^{-1}$, KBr) 2870, 2810, 2050, 1490, 1440.

NMR: $^1$H (500 MHz, CDCl$_3$; 27° C.) δ(ppm) 7.25–7.35 (10H, m), 5.69–5.82 (1H, m), 5.35–5.43 (1H, m), 4.30–4.74 (4H, m), 3.89 (0.3H, dd, J=5.5, 8.5 Hz), 3.55–3.70 (3.7H, m), 1.97–2.10 (2H, m), 1.25–1.36 (22H, m), 0.88 (3H, t, J=6.8 Hz).

(v) Synthesis of Compound A7

To a solution of 0.45 g of the azide (Compound A5) in 10 ml of tetrahydrofuran were added 2 ml of a 10% methanolic hydrochloric acid solution and 0.25 g of palladium black. The reactor was purged with hydrogen and stirred at room temperature for 12 hours, filtered through celite and concentrated to give 301 mg of an amine as white powder (Compound A6). To this product were added 5 ml of tetrahydrofuran and 523 mg of p-nitro-phenyl myristate, and the mixture was stirred at 55° C. for 20 hours. After concentration, the concentrate was diluted with ethyl acetate and washed thrice with a saturated aqueous sodium hydrogen carbonate. After further washed with brine, the ethyl acetate layer was concentrated and purified on a silica gel column (Wako Gel C-200, 20 g, chloroform:methanol=20:1) to give an amide (Compound A7) in an amount of 280 mg (yield 54.8%).

$[\alpha]^{24}_D$=+3.5° (Py, c=1.87).

MS: FDMS 513.

mp: 104°–105° C.

NMR: $^1$H (500 MHz, C$_5$D$_5$N; 27° C.) δ(ppm) 8.35 (1H, d, J=9.2 Hz), 6.36 (1H, t, J=4.9 Hz), 6.24 (1H, d, J=6.1 Hz), 4.62–4.67 (1H, m), 4.46 (1H, dt, J=4.9, 11.0 Hz), 4.25–4.33 (2H, m), 2.47 (2H, dt, J=1.8, 7.3 Hz), 1.25–1.95 (50H, m), 0.88 (6H, t, J=6.7 Hz).

(vi) Synthesis of Compounds A9 and A10

With 100 mg of the amide (Compound A7) were mixed 4.5 ml of tetrahydrofuran and 400 mg of powdery Molecular Sieves 4A, and the mixture was stirred for 10 minutes. A 124 mg of stannous chloride and 136 mg of silver perchlorate were added, and the mixture was further stirred for 30 minutes. After cooling the mixture to −10° C., a solution of 106 mg of benzylglucosyl fluoride (Compound A8) in 1.5 ml of tetrahydrofuran was added. The mixture was slowly raised to room temperature, stirred for 30 minutes and filtered through celite. The filtrate was extracted with a small amount of acetone. The extract was concentrated and purified on a silica gel column (Wako Gel C-200, 12 g, hexane:acetone=3:1) to give a glucoside (mixture of Compounds A9 and A10) in an amount of 101 mg (yield 50.4%).

(vii) Synthesis of Compounds A11 and A12

To 100 mg of the glucoside (mixture of Compounds A9 and A10) were added 3 ml of tetrahydrofuran and 10 mg of palladium black, and the reactor was purged with hydrogen and stirred at room temperature for 16 hours. The catalyst was removed by filtration, and the filtrate was concentrated to give a mixture of Compounds A13 and A14.

The mixture was dissolved in 2.0 ml of pyridine, 0.5 ml of acetic anhydride was added, and the resulting mixture was stirred at room temperature for 16 hours. After adding a small amount of ethanol, the mixture was stirred and concentrated. After adding a small amount of toluene, the mixture was concentrated and purified on a silica gel column (Wako Gel C-200, 10 g, hexane:ethyl acetate=3:1) to give separately Compound A11 and Compound A12 in an amount of 19.3 mg and 12.6 mg, respectively.

Data of Compound A11

MS: FDMS 884.

NMR: $^1$H (500 MHz, CDCl$_3$; 27° C.) δ(ppm) 5.99 (1H, d, J=9.2 Hz), 5.19 (1H, t, J=9.5 Hz), 5.07 (1H, t, J=9.8 Hz), 4.94 (1H, dd, J=8.2, 9.5 Hz), 4.86 (1H, dt, J=4.9, 7.9 Hz), 4.46 (1H, d, J=7.9 Hz), 4.26 (1H, m), 4.24 (1H, dd, J=4.3, 12.2 Hz), 4.15 (1H, dd, J=2.1, 12.5 Hz), 3.91 (1H, dd, J=3.7, 9.8 Hz), 3.69 (1H, ddd, J=2.4, 4.6, 10.1 Hz), 3.59 (1H, dd, J=4.3, 10.4 Hz), 2.16 (2H, t, J=7.6 Hz), 2.09, 2.05, 2.04, 2.03 & 2.01 (each 3H, s), 1.50–1.70 (6H, m), 1.20–1.40 (44H, m), 0.88 (6H, t, J=6.7 Hz).

Data of Compound A12

MS: FDMS 884.

NMR: $^1$H (500 MHz, CDCl$_3$; 27° C.) δ(ppm) 5.94 (1H, d, J=9.2 Hz), 5.47 (1H, t, J=9.8 Hz), 4.93–5.01 (3H,m), 4.89 (1H, dd, J=3.7, 10.4 Hz), 4.32 (1H, m), 4.21 (1H, dd, J=4.9, 12.8 Hz), 4.10 (1H, dd, J=1.8, 12.2 Hz), 3.97 (1H, ddd, J=2.4, 4.9, 10.4 Hz), 3.70 (1H, dd, J=3.7, 10.4 Hz), 3.49 (1H, dd, J=3.7, 10.4 Hz), 2.23 (2H, dt, J=3.1, 7.6 Hz), 2.093, 2.085, 2.06, 2.03 & 2.02 (each 3H, s), 1.50–1.70 (6H, m), 1.10–1.40 (44H, m), 0.88 (6H, t, J=6.7 Hz).

(viii) Synthesis of Compound A13

To 19.2 mg of the pentaacetate (Compound A11) were added 4 ml of methanol and 0.1 ml of a 1N methanolic sodium methoxide solution, and the mixture was left standing for 3 minutes. A resin (DOWEX 50W X8, The Dow Chemical Company) was added to adjust pH to 7 and filtered. The collected solids were sufficiently washed with chloroform-methanol (1:1), and the filtrate and washings were concentrated and purified on silica gel column (Wako Gel C-200, 8 g, chloroform:methanol=8:1) to give Compounds 7 (A13) in an amount of 9.5 mg (yield 64.9%).

Data of Compound 7

$[\alpha]^{23}_D$ =−3.1° (Py, c=0.85).

MS: FDMS 675.

IR: (cm$^{-1}$, KBr) 3280, 2910, 2840, 1635, 1540, 1465, 1370, 1070.

mp: 159.0°–162.5° C.

NMR: $^1$H (500 MHz, C$_5$D$_5$N; 27° C.) δ(ppm) 8.40 (1H, d, J=8.5 Hz), 6.44 (1H, m), 6.29 (1H, m), 4.97 (1H, d, J=7.9 Hz), 4.78 (1H, dd, J=4.9, 10.4 Hz), 4.72 (1H, m), 4.55 (1H, d, J=11.6 Hz), 4.36 (1H, dd, J=5.5, 11.6 Hz), 4.18–4.30 (4H), 4.06 (1H, t, J=7.9 Hz), 3.97 (1H, m), 2.47 (2H, t, J=7.3 Hz), 1.78–1.99 (4H, m), 1.58 (1H, m), 1.06–1.44 (45H, m), 0.88 (6H, t, J=7.0 Hz).

$^{13}$C (125 MHz, C$_5$D$_5$N; 27° C.) δ(ppm) 173.3 (s), 106.0 (d), 78.6 (d), 75.3 (d), 71.7 (d), 71.4 (d), 70.9 (d), 62.8 (t), 55.1 (d), 36.9 (t), 34.9 (t), 32.1 (t), 30.2 (t), 30.1 (t), 30.02 (t), 29.97 (t), 29.9 (t), 29.8 (t), 29.7 (t), 29.6 (t), 29.5 (t), 26.5 (t), 26.4 (t), 22.9 (t), 14.3 (q).

(ix) Synthesis of Compound A14

To 12.5 mg of the pentaacetate (Compound A12) were added 3 ml of methanol and 0.1 ml of a 1N methanolic sodium methoxide solution, and the mixture was left standing for 5 minutes. A resin (DOWEX 50W X8, The Dow Chemical Company) was added to adjust pH to 7 and filtered. The collected solids were sufficiently washed with chloroform-methanol (1:1), and the filtrate and washings were concentrated and purified on silica gel column (Wako Gel C-200, 8 g, chloroform:methanol=10:1) to give Compounds 8 (A14) in an amount of 5.6 mg (yield 58.9%).

Data of Compound 8

$[\alpha]^{23}_D$=+57.4° (Py, c=0.46).

MS: FDMS 675.

IR: (cm$^{-1}$, KBr) 3300, 2910, 2850, 1640, 1545, 1470, 1375, 1150, 1025.

mp: 162.0°–163.0 ° C.

NMR: $^1$H (500 MHz, C$_5$D$_5$N; 27° C.) δ(ppm) 8.43 (1H, d, J=8.6 Hz), 7.04 (1H, m), 7.00 (1H, m), 6.76 (1H, m), 6.28 (1H, m), 6.13 (1H, m), 5.40 (1H, d, J=3.1 Hz), 4.69 (1H, m), 4.22–4.60 (7H, m), 4.10–4.21 (2H, m), 2.43 (2H, t, J=7.3 Hz), 1.76–1.93 (4H, m), 1.52 (1H, m), 1.10–1.42 (45H, m), 0.88 (6H, t; J=6.7 Hz).

$^{13}$C (125 MHz, C$_5$D$_5$N; 27° C.) δ(ppm) 173.4 (s), 101.8 (d), 75.4 (d), 74.6 (d), 73.8 (d), 72.0 (d), 71.7 (d), 69.6 (t), 62.8 (t), 55.0 (d), 36.8 (t), 35.1 (t), 32.1 (t), 30.2 (t), 30.1 (t), 30.03 (t), 29.98 (t), 29.94 (t), 29.88 (t), 29.81 (t), 29.75 (t), 29.6 (t), 26.6 (t), 26.4 (t), 22.9 (t), 14.3 (q).

In the synthesis of Compound 7 in Route A, the α and β derivatives were prepared by reacting thiogalactoside protected with benzyl group, N-iodosuccinimide and trifluoromethanesulfonic acid in place of reacting the ceramide A7 with benzylglucosyl fluoride (Compound A8). These derivatives were further subjected to the reactions according to Route A and separated to give Compound 9.

Data of Compound 9

$[\alpha]^{23}_D$=+7.3° (Py, c=0.93).

MS: FDMS 675.

IR: (cm$^{-1}$, KBr) 3290, 2920, 2860, 1645, 1550, 1470, 1375, 1290, 1075.

mp: 175.0°–177.0° C.

NMR: $^1$H (500 MHz, C$_5$D$_5$N; 27° C.) δ(ppm) 8.31 (1H, d, J=9.2 Hz), 4.88 (1H, d, J=7.3 Hz), 4.80 (1H, dd, J=4.9, 10.4 Hz), 4.67 (1H, m), 4.55 (1H, d, J=3.1 Hz), 4.49 (1H, dd, J=7.9, 9.2 Hz), 4.40–4.45 (2H, m), 4.10–4.25 (3H, m), 4.06 (1H, t, J=5.8 Hz), 2.44 (2H, t, J=7.3 Hz), 1.76–1.92 (4H, m), 1.53 (1H, m), 1.10–1.42 (45H, m), 0.88 (6H, t, J=6.7 Hz).

$^{13}$C (125 MHz, C$_5$D$_5$N; 27° C.) δ(ppm) 173.3 (s), 106.5 (d), 77.1 (d), 75.4 (d), 72.7 (d), 71.2 (d), 70.7 (d), 70.2 (t), 62.4 (t), 55.1 (d), 36.9 (t), 34.9 (t), 32.1 (t), 30.2 (t), 30.1 (t), 30.01 (t), 29.97 (t), 29.9 (t), 29.8 (t), 29.7 (t), 29.6 (t), 29.5 (t), 26.4 (t), 23.1 (t), 22.9 (t), 14.3 (q).

In the synthesis of Compound 7 in Route A, tridecanetriphenylphosphonium bromide instead of tetradecanetriphenylphosphonium bromide was reacted with the aldehyde A2. Further, p-nitrophenyl octadecanoate in place of p-nitrophenyl myristate was reacted with the amine obtained by reduction, and the reaction was continued in accordance with Route A to give the ceramide. An excessive amount of benzylgalactosyl fluoride was added to the ceramide to give a compound having two galactose units, which was further subjected to deprotection to give the aimed compound 6.

Data of Compound 6

$[\alpha]^{23}_D$ =+59.8° (Py, c=0.33).

MS: FDMS 962.

IR: (cm$^{-1}$, KBr) 3400, 2910, 2840, 1540, 1465, 1140, 1060.

mp: 169°–171° C.

NMR: $^1$H (500 MHz, C$_5$D$_5$N; 27° C.) δ(ppm) 8.75 (1H, d, J=9.2 Hz), 5.63 (1H, d, J=4.3 Hz), 5.44 (1H, d, J=3.7 Hz), 4.94 (1H, m), 4.71 (2H, m), 4.63 (1H, dd, J=4.1, 10.4 Hz), 4.36–4.61 (10H, m), 4.23 (1H, dd, J=7.8, 9.9 Hz), 4.18 (1H, m), 2.44 (2H, dd, J=6.7, 7.3 Hz), 2.02 (1H, m), 1.92 (1H, m), 1.83 (2H, m), 1.75 (1H, m), 1.60 (1H, m), 1.16–1.36 (62H, m), 0.86 (6H, t, J=6.7 Hz).

$^{13}$C (125 MHz, C$_5$D$_5$N; 27° C.) δ(ppm) 173.1 (s), 103.7 (d), 101.6 (d), 83.7 (d), 73.0 (d), 73.0 (d), 71.7 (d), 71.5 (d), 71.1 (d), 70.9 (d), 70.9 (d), 70.6 (d), 68.4 (t), 62.8 (t), 62.4 (t), 52.6 (d), 36.9 (t), 33.2 (t), 32.0 (t), 30.2 (t), 30.1 (t), 30.0 (t), 29.9 (t), 29.8 (t), 29.6 (t), 26.3 (t), 25.9 (t), 22.9 (t), 14.2 (q).

In the synthesis of Compound 7 in Route A, tribenzylxylofuranosyl fluoride instead of tetrabenzylglucosyl fluoride was reacted with the ceramide A7, and the reaction was continued in accordance with Route A to give the α-xylofuranoside derivative 10. The same compound was prepared by the similar reactions to those described above starting from the sphingosine B1.

Data of Compound 10

[α]$^{23}_D$=+49.7° (Py, c=0.35).

MS: FDMS 645.

IR: (cm$^{-1}$, KBr) 3320, 2920, 2850, 1650, 1635, 1535, 1465, 1125, 1030.

mp: 101.5°–105.0° C.

NMR: $^1$H (500 MHz, C$_5$D$_5$N; 27° C.) δ(ppm) 8.42 (1H, d, J=8.6 Hz), 7.11 (1H, m), 6.41 (1H, m), 6.23 (1H, m), 5.49 (1H, d, J=4.3 Hz), 4.81 (1H, m), 4.72 (2H, m), 4.46 (1H, dd, J=3.3, 10.1 Hz), 4.38 (1H, dd, J=4.3, 11.6 Hz), 4.32 (2H, m), 4.22 (1H, m), 2.42 (2H, t, J=7.3 Hz), 1.75–1.95 (5H, m), 1.54 (1H, m), 1.00–1.42 (44H, m), 0.88 (6H, t, J=7.0 Hz).

$^{13}$C (125 MHz, C$_5$D$_5$N; 27° C.) δ(ppm) 173.2 (s), 103.3 (d), 80.2 (d), 79.4 (d), 77.1 (d), 71.8 (d), 69.1 (t), 62.3 (t), 54.7 (d), 36.8 (t), 35.0 (t), 32.1 (t), 30.2 (t), 30.1 (t), 30.00 (t), 29.96 (t), 29.93 (t), 29.87 (t), 29.8 (t), 29.7 (t), 29.6 (t), 26.6 (t), 26.4 (t), 22.9 (t), 14.3 (q).

In the synthesis of Compound 7 in Route A, tribenzylxylopyranosyl fluoride instead of tetrabenzylglucosyl fluoride was reacted with the ceramide A7, and the reaction was continued in accordance with Route A to give the β-xylopyranoside derivative 11. The same compound was prepared by the similar reactions to those described above starting from the sphingosine B1.

Data of Compound 11

[α]$^{24}_D$=−7.4° (Py, c=0.19).

MS: FDMS 645.

IR: (cm$^{-1}$, KBr) 3360, 2940, 2870, 1625, 1540, 1470, 1170, 1095, 1070.

mp: 142.0°–146.0° C.

NMR:$^1$H (500 MHz, C$_5$D$_5$N; 27° C.) δ(ppm) 8.39 (1H, d, J=8.5 Hz), 7.32 (1H, m), 7.11 (1H, m), 6.28 (1H, m), 4.84 (1H, d, J=7.9 Hz), 4.70–4.78 (2H, m), 4.32 (1H, dd, J=5.2, 11.3 Hz), 4.14–4.27 (3H, m), 4.13 (1H, t, J=8.6 Hz), 4.02 (1H, t, J=8.2 Hz), 3.67 (1H, t, J=10.7 Hz), 2.45 (2H, t, J=7.3 Hz), 1.80–1.95 (4H, m), 1.55 (1H, m), 1.19–1.43 (45H, m), 0.88 (6H, t, J=6.7 Hz).

$^{13}$C (125 MHz, C$_5$D$_5$N; 27° C.) δ(ppm) 173.3 (s), 106.2 (d), 78.4 (d), 75.0 (d), 71.5 (d), 71.0 (d), 70.5 (t), 67.3 (t), 54.9 (d), 36.9 (t), 35.0 (t), 32.1 (t), 30.2 (t), 30.1 (t), 30.01 (t), 29.99 (t), 29.93 (t), 29.83 (t), 29.7 (t), 29.6 (t), 26.5 (t), 26.4 (t), 22.9 (t), 14.3 (q).

In the synthesis of Compound 7 in Route A, tribenzyl-6-deoxygalactopyranosyl fluoride instead of tetrabenzylglucosyl fluoride was reacted with the ceramide A7, and the reaction was continued in accordance with Route A to give the α-galactopyranoside derivative 12 and the β-galactopyranoside derivative 13. The same compounds were prepared by the similar reactions to those described above starting from the sphingosine B1.

Data of Compound 12

[α]$^{23}_D$=+64.6° (Py, c=1.0).

MS: FDMS 659.

IR: (cm$^{-1}$, KBr) 3270, 3080, 2910, 2850, 1635, 1570, 1470, 1370, 1340, 1295, 1160, 1130, 1070, 1035.

mp: 143.0°–144.5° C.

NMR: $^1$H (500 MHz, C$_5$D$_5$N; 27° C.) δ(ppm) 8.48 (1H, d, J=8.5 Hz), 6.12 (1H, m), 5.36 (1H, d, J=3.7 Hz), 4.73 (1H, m), 4.57 (1H, m), 4.34–4.49 (3H, m), 4.23–4.30 (2H, m), 4.11 (1H, bs), 2.47 (2H, t, J=7.3 Hz), 1.80–1.94 (4H, m), 1.58 (1H, m), 1.55 (3H, d, J=6.7 Hz), 1.39 (2H, m), 1.19–1.33 (43H, m), 0.88 (6H, t, J=7.0 Hz).

$^{13}$C (125 MHz, C$_5$D$_5$N; 27° C.) δ(ppm) 173.2 (s), 101.7 (d), 73.2 (d), 71.9 (d), 71.6 (d), 70.1 (d), 69.2 (t), 67.5 (d), 54.7 (d), 36.8 (t), 35.1 (t), 32.1 (t), 30.2 (t), 30.0 (t), 29.71 (t), 29.6 (t), 26.6 (t), 26.4 (t), 22.9 (t), 17.2 (q), 14.3 (q), 14.2 (q).

Data of Compound 13

[α]$^{23}_D$=+3.8° (Py, c=0.52).

MS: FDMS 659.

IR: (cm$^{-1}$, KBr) 3260, 2900, 2840, 1640, 1545, 1465, 1370, 1280, 1160, 1125, 1070.

mp: 137.5°–139.5 ° C.

NMR: $^1$H (500 MHz, C$_5$D$_5$N; 27° C.) δ(ppm) 8.32 (1H, d, J=8.5 Hz), 6.70 (1H, m), 6.27 (1H, m), 4.81 (1H, dd, J=5.5, 10.4 Hz), 4.78 (1H, d, J=7.3 Hz), 4.71 (1H, m), 4.40 (1H, dd, J=7.9, 9.2 Hz), 4.22 (1H, dd, J=3.1, 10.4 Hz), 4.16 (1H, m), 4.09 (1H, dd, J=3.4, 9.5 Hz), 4.05 (1H, bd, J=3.1 Hz), 3.82 (1H, q, J=6.4 Hz), 2.43 (2H, t, J=7.3 Hz), 1.79–1.93 (4H, m), 1.55 (3H, d, J=6.1 Hz), 1.53 (1H, m), 1.20–1.42 (45H, m), 0.88 (6H, t, J=6.7 Hz).

$^{13}$C (125 MHz, C$_5$D$_5$N; 27° C.) δ(ppm) 173.3 (s), 106.1 (d), 75.4 (d), 72.6 (d), 72.3 (d), 71.6 (d), 71.3 (d), 70.5 (t), 55.0 (d), 36.9 (t), 34.9 (t), 32.1 (t), 30.2 (t), 30.1 (t), 30.01 (t), 29.99 (t), 29.9 (t), 29.8 (t), 29.7 (t), 29.6 (t), 26.5 (t), 26.4 (t), 22.9 (t), 17.3 (q), 14.3 (q).

In the synthesis of Compound 7 in Route A, tribenzyl-6-deoxygalactofuranosyl fluoride instead of tetrabenzylglucosyl fluoride was reacted with the ceramide A7, and the reaction was continued in accordance with Route A to give the α-galactofuranoside derivative 14 and the β-galactofuranoside derivative 15. The same compounds were prepared by the similar reactions to those described above starting from the sphingosine B1.

Data of Compound 14

[α]$^{23}_D$=+33.3° (Py, c=1.29).

MS: FDMS 659.

IR: (cm$^{-1}$, KBr) 3300, 2920, 2850, 1640, 1545, 1470, 1375, 1280, 1130, 1025, 1005.

mp: 100.0°–100.5° C.

NMR: $^1$H (500 MHz, C$_5$D$_5$N; 27° C.) δ(ppm) 8.51 (1H, d, J=8.5 Hz), 7.42 (1H, m), 6.72 (1H, m), 6.22 (1H, m), 6.12 (1H, m), 5.31 (1H, d, J=4.3 Hz), 4.85 (1H, t, J=7.9 Hz), 4.62–4.69 (2H, m), 4.41 (1H, dd, J=4.0, 10.1 Hz), 4.37 (1H, m), 4.33 (1H, dd, J=3.1, 9.8 Hz), 4.25 (1H, m), 4.18 (1H, dd, J=5.5, 6.7 Hz), 2.50 (2H, t, J=7.3 Hz), 1.79–1.94 (4H, m), 1.58 (3H, d, J=6.1 Hz), 1.51 (1H, m), 1.19–1.42 (45H, m), 0.88 (6H, t, J=6.7 Hz).

$^{13}$C (125 MHz, C$_5$D$_5$N; 27° C.) δ(ppm) 173.3 (s), 103.5 (d), 87.4 (d), 79.4 (d), 76.1 (d), 71.6 (d), 69.5 (t), 68.7 (d), 54.7 (d), 36.8 (t), 35.1 (t), 32.1 (t), 30.2 (t), 30.1 (t), 30.00 (t), 29.96 (t), 29.92 (t), 29.89 (t), 29.84 (t), 29.78 (t), 29.6 (t), 26.6 (t), 26.4 (t), 22.9 (t), 20.2 (q), 14.3 (q).

Data of Compound 15

[α]$^{23}_D$=−30.8° (Py, c=2.0).

MS: FDMS 659.

IR: (cm$^{-1}$, KBr) 3260, 2900, 2840, 1650, 1560, 1465, 1370, 1280, 1070, 1005.

mp: 101.0°–103.0° C.

NMR: $^1$H (500 MHz, C$_5$D$_5$N; 27° C.) δ(ppm) 8.46 (1H, d, J=8.5 Hz), 5.53 (1H, s), 4.68–4.77 (3H, m), 4.53 (1H, dd, J=5.8, 10.1 Hz), 4.47 (1H, t, J=4.6 Hz), 4.36 (1H, dq, J=4.0, 6.4 Hz), 4.15 (1H, dd, J=6.1, 11.6 Hz), 4.12 (1H, dd, J=3.4, 10.1 Hz), 2.47 (2H, t, J=7.3 Hz), 1.78–1.92 (5H, m), 1.85 (3H, d, J=6.7 Hz), 1.55 (1H, m), 1.19–1.43 (44H, m), 0.88 (6H, t, J=7.0 Hz).

$^{13}$C (125 MHz, C$_5$D$_5$N; 27° C.) δ(ppm) 173.3 (s), 109.2 (d), 89.5 (d), 82.6 (d), 78.9 (d), 72.0 (d), 67.7 (t), 67.4 (d), 54.1 (d), 36.8 (t), 35.0 (t), 32.1 (t), 30.1 (t), 30.0 (t), 29.94 (t), 29.90 (t), 29.86 (t), 29.8 (t), 29.7 (t), 29.6 (t), 26.5 (t), 26.4 (t), 22.9 (t), 20.4 (q), 14.3 (q).

In the synthesis of Compound 7 in Route A, triacetyl-2-deoxygalactopyranosyl bromide and tetraethylammonium bromide instead of tetrabenzylglucosyl fluoride was reacted with the ceramide A7 to give a glycosyl derivative, which was next deprotected with sodium methylate to give the α-galactopyranoside derivative 16. The same compound was prepared by the similar reactions to those described above starting from the sphingosine B1.

Data of Compound 16

$[\alpha]^{23}_D$=+40.9° (Py, c=1.63).

MS: FDMS 659, 513, 147.

IR: (cm$^{-1}$, KBr) 3270, 2910, 2840, 1640, 1555, 1465, 1065, 1025.

mp: 133.0°–134.0° C.

NMR: $^1$H (500 MHz, C$_5$D$_5$N; 27° C.) δ(ppm) 8.52 (1H, m), 6.28 (1H, m), 5.26 (1H, bs), 4.75 (1H, m), 4.53 (1H, m), 4.35–4.49 (5H, m), 4.18–4.27 (2H, m), 2.51 (3H, m), 2.21 (1H, m), 1.82–2.00 (5H, m), 1.60 (1H, m), 1.10–1.45 (44H, m), 0.88 (6H, t, J=6.7 Hz).

$^{13}$C (125 MHz, C$_5$D$_5$N; 27° C.) δ(ppm) 173.4 (s), 99.5 (d), 72.9 (d), 71.7 (d), 69.6 (d), 67.7 (d), 66.2 (t), 63.8 (t), 55.1 (d), 36.8 (t), 35.0 (t), 34.3 (t), 32.1 (t), 30.2 (t), 30.1 (t), 30.00 (t), 29.97 (t), 29.91 (t), 29.87 (t), 29.8 (t), 29.7 (t), 29.6 (t), 26.6 (t), 26.5 (t), 22.9 (t), 14.3 (q).

In the synthesis of Compound 7 in Route A, tribenzyl-L-arabinopyranosyl fluoride instead of tetrabenzylglucosyl fluoride was reacted with the ceramide A7, and the reaction was continued in accordance with Route A to give the β-L-arabinopyranoside derivative 17 and the α-L-arabinopyranoside derivative 18. The same compounds were prepared by the similar reactions to those described above starting from the sphingosine B1.

Data of Compound 17

$[\alpha]^{24}_D$=+65.7° (Py, c=1.23).

MS: FDMS 644.

IR: (cm$^{-1}$, KBr) 3280, 2910, 2850, 1640, 1545, 1470, 1375, 1340, 1140, 1070, 1000.

mp: 111.0°–113.0° C.

NMR: $^1$H (500 MHz, C$_5$D$_5$N; 27° C.) δ(ppm) 8.45 (1H, d, J=8.6 Hz), 5.40 (1H, d, J=3.1 Hz), 4.71 (1H, m), 4.59 (1H, dd, J=3.4, 9.5 Hz), 4.44 (2H, m), 4.33 (1H, bs), 4.20–4.28 (3H, m), 4.06 (1H, dd, J=2.1, 11.9 Hz), 2.45 (2H, t, J=7.3 Hz), 1.80–1.93 (4H, m), 1.56 (1H, m), 1.19–1.42; (45H, m), 0.88 (6H, t, J=6.7 Hz).

$^{13}$C (125 MHz, C$_5$D$_5$N; 27° C.) δ(ppm) 173.2 (s), 102.0 (d), 71.9 (d), 70.9 (d), 70.5 (d), 70.1 (d), 69.2 (t), 64.5 (t), 54.7 (d), 36.8 (t), 35.1 (t), 32.1 (t), 30.2 (t), 30.1 (t), 30.00 (t), 29.96 (t), 29.93 (t), 29.87 (t), 29.8 (t), 29.7 (t), 29.6 (t), 26.6 (t), 26.4 (t), 22.9 (t), 14.3 (q).

Data of Compound 18

$[\alpha]^{24}_D$=+6.7° (Py, c=1.28).

MS: FDMS 644.

IR: (cm$^{-1}$, KBr) 3370, 2920, 2850, 1620, 1530, 1470, 1420, 1255, 1090, 1070, 1005.

mp: 126.0°–129.0° C.

NMR: $^1$H (500 MHz, C$_5$D$_5$N; 27° C.) δ(ppm) 8.30 (1H, d, J=8.5 Hz), 6.28 (1H, m), 4.78 (1H, d, J=6.7 Hz), 4.75 (1H, m), 4.70 (1H, m), 4.45 (1H, t, J=7.6 Hz), 4.28–4.32 (2H, m), 4.10–4.20 (3H, m), 3.75 (1H, bd, J=11.0 Hz), 2.43 (2H, t, J=7.3 Hz), 1.78–1.93 (4H, m), 1.53 (1H, m), 1.20–1.41 (45H, m), 0.88 (6H, t, J=7.0 Hz).

$^{13}$C (125 MHz, C$_5$D$_5$N; 27° C.) δ(ppm) 173.3 (s), 105.8 (d), 74.5 (d), 72.5 (d), 71.5 (d), 70.0 (d), 69.2 (t), 66.8 (t), 54.7 (d), 36.9 (t), 35.0 (t), 32.1 (t), 30.2 (t), 30.00 (t), 29.97 (t), 29.9 (t), 29.8 (t), 29.7 (t), 29.6 (t), 26.5 (t), 26.4 (t), 22.9 (t), 14.3 (q), 14.2 (q).

(2) Synthetic Route B: Synthesis of Compounds 4 and 5

(i) Synthesis of Compound B2

To 75 mg of sphingosine (compound B1) were added 4.0 ml of tetrahydrofuran, 170 mg of p-nitrophenyl (R)-2-acetoxymyristate and 7.6 mg of 4-dimethylaminopyridine, and the mixture was stirred at 40° C. for 16 hours, directly concentrated and purified on a silica gel column (Wako Gel C-200, 20 g, chloroform:acetone=4:1) to give an amide (Compound B2) in an amount of 108.4 mg (yield 49.4%).

NMR: $^1$H (500 MHz, C$_5$D$_5$N; 27° C.) δ(ppm) 6.76 (1H, d, J=7.9 Hz), 5.79 (1H, dt, J=7.6, 15.3 Hz), 5.51 (1H, dd, J=6.4, 15.6 Hz), 5.08 (1H, dd, J=4.9, 7.3 Hz), 4.33 (1H, m), 3.97 (1H, dd, J=3.4, 11.3 Hz), 3.84 (1H, m), 3.67 (1H, dd, J=3.4, 11.3 Hz), 2.14 (3H, s), 2.04 (4H, m), 1.82 (2H, m), 1.1–1.4 (60H, m), 0.87 (6H, t, J=6.7 Hz).

(ii) Synthesis of Compounds B4 and B5

To 108 mg of the amide (Compound B2) were added 3.0 ml of tetrahydrofuran and 400 mg of powdery Molecular Sieves 4A, and the mixture was stirred for 10 minutes. After 68.3 mg of stannous chloride and 74.6 mg of silver perchlorate were added, the mixture was further stirred for 30 minutes. After cooling the mixture to −10° C., a solution of 249 mg of benzylgalactosyl fluoride (Compound B3) in 1.5 ml of tetrahydrofuran was added. After 30 minutes, the mixture was raised to room temperature, stirred for 1 hour and filtered through celite. The residue was washed with a small amount of chloroform-methanol (1:1). The filtrate and washings were concentrated and purified on a silica gel column (Wako Gel C-200, 20 g, hexane:acetone=4:1) to give a galactoside (mixture of Compounds B4 and B5) in an amount of 90.0 mg (yield 33.7%).

(iii) Synthesis of Compounds B6 and B7

To 90 mg of the galactoside (mixture of Compounds B4 and B5) were added 2.0 ml of tetrahydrofuran and 20 mg of palladium black, and the mixture was purged with hydrogen and stirred at room temperature for 16 hours. The mixture was filtered through celite, and the filtrate was concentrated to give a mixture of Compounds B8 and B9. Pyridine (3.0 ml) and acetic anhydride (0.5 ml) were added, and the mixture was left standing at room temperature for 16 hours, concentrated, and azeotropically distilled with toluene. Purification on a silica gel column (Wako Gel C-200, 10 g, hexane:ethyl acetate=4:3) gave separately Compound B6 Compound B7 in an amount of 37.7 mg and 13.3 mg, respectively.

Data of Compound B6

MS: FDMS 1372.

NMR: $^1$H (500 MHz, CDCl$_3$; 27° C.) δ(ppm) 6.25 (1H, d, J=9.2 Hz), 5.48 (1H, d, J=2.4 Hz), 5.42 (1H, bs), 5.29 (1H, dd, J=3.1, 11.0 Hz), 5.24 (2H, bs), 5.21 (1H, d, J=3.7 Hz), 5.14 (1H, d, J=3.7 Hz), 5.12 (1H, t, J=3.7 Hz), 4.93 (1H, m), 4.26–4.33 (2H, m), 4.03–4.12 (5H, m), 3.87 (1H, m), 3.74 (1H, dd, J=3.1, 10.4 Hz), 3.61 (1H, dd, J=3.4, 10.1 Hz), 2.21, 2.14, 2.13, 2.10 & 2.09 (each 3H, s), 2.06 (6H, s), 1.99 & 1.98 (each 3H, s), 1.82 (2H, m), 1.65 (2H, m), 1.1–1.5 (66H, m), 0.88 (6H, t, J=6.7 Hz).

Data of Compound B7

MS: FDMS 1372.

NMR: $^1$H (500 MHz, CDCl$_3$; 27° C.) δ(ppm) 6.70 (1H, d, J=8.5 Hz), 5.45 (2H, dd, J=3.1, 12.2 Hz), 5.26 (1H, dd, J=3.4, 10.7 Hz), 5.12–5.18 (2H, m), 5.09 (1H, d, J=3.1 Hz), 5.05 (1H, dd, J=3.7, 10.4 Hz), 4.90 (1H, t, J=6.4 Hz), 4.52 (1H, d, J=7.9 Hz), 4.43 (1H, dd, J=7.0, 11.3 Hz), 4.08–4.21 (5H, m), 4.03 (1H, t, J=6.4 Hz), 3.77 (1H, dd, J=6.1, 10.4 Hz), 3.65 (1H, m), 3.51 (1H, dd, J=6.7, 10.7 Hz), 2.18, 2.15, 2.14 (each 3H, s), 2.062 & 2.058 (each 6H, s), 2.00 & 1.97 (each 3H, S), 1.80 (2H, m), 1.61 (4H, m), 1.1–1.46 (64H, m), 0.88 (6H, t, J=6.7 Hz).

(ix) Synthesis of Compound B8

To 36.3 mg of the nonaacetate (Compound B6) were added 1 ml of methanol and 0.1 ml of a 1N methanolic sodium methoxide solution, and the mixture was left standing for 5 minutes. A resin (DOWEX 50W X8, The Dow Chemical Company) was added to adjust pH to 7 and filtered. The collected solids were sufficiently washed with chloroform-methanol (1:1), the filtrate and washings were concentrated and purified on silica gel column (Wako Gel C-200, 8 g, chloroform:methanol=4:1) to give Compounds 4 (B8) in an amount of 20.6 mg (yield 88.5%).

Data of Compound 4

$[\alpha]^{25}_D$=+80.6° (Py, c=1.0).

MS: FDMS 993.

IR: (cm$^{-1}$, KBr) 3330, 2900, 2830, 1635, 1520, 1460, 1335, 1140, 1065, 1020.

mp: 122°–132 ° C. (broad).

NMR: $^1$H (500 MHz, $C_5D_5N$; 27° C.) δ(ppm) 8.57 (1H, d, J=9.8 Hz), 7.36 (1H, m), 6.1–6.8 (m), 5.78 (1H, d, J=3.7 Hz), 5.46 (1H, d, J=3.1 Hz), 4.94 (1H, m), 4.72 (2H, m), 4.58–4.67 (3H, m), 4.38–4.58 (8H, m), 4.28–4.38 (3H, m), 2.17 (1H, m), 1.95–2.12 (2H, m), 1.66–1.99 (3H, m), 1.20–1.50 (64H, m), 0.882 (3H, t, J=6.7 Hz), 0.876 (3H, t, J=6.7 Hz).

$^{13}$C (125 MHz, $C_5D_5N$; 27° C.) δ(ppm) 175.3 (s), 103.3 (d), 101.4 (d), 81.7 (d), 73.1 (d), 72.9 (d), 72.5 (d), 71.6 (d), 71.5 (d), 71.1 (d), 71.0 (d), 70.8 (d), 70.5 (d), 68.5 (t), 62.9 (t), 62.5 (t), 52.1 (d), 35.7 (t), 32.9 (t), 32.13 (t), 32.10 (t), 30.5 (t), 30.2 (t), 30.0 (t), 29.9 (t), 29.62 (t), 29.59 (t), 25.8 (t), 25.4 (t), 22.9 (t), 14.3 (q).

(ix) Synthesis of Compound B9

To 13.3 mg of the nonaacetate (Compound B7) were added 1 ml of methanol and 0.1 ml of a 1N methanolic sodium methoxide solution, and the mixture was left standing for 5 minutes. A resin (DOWEX 50W X8, The Dow Chemical Company) was added to adjust pH to 7 and filtered. The collected solids were sufficiently washed with chloroform-methanol (1:1), the filtrate and washings were concentrated and purified on silica gel column (Wako Gel C-200, 6 g, chloroform:methanol=4:1) to give Compounds 5 (B9) in an amount of 5.8 mg (yield 60.2%).

Data of Compound 5

$[\alpha]^{25}_D$=+44.3° (Py, c=0.42).

MS: FDMS 993.

IR: (cm$^{-1}$, KBr) 3340, 2890, 2810, 1630, 1525, 1460, 1140, 1060.

mp: 196°–204° C. (broad).

NMR: $^1$H (500 MHz, $C_5D_5N$; 27° C.) δ(ppm) 8.64 (1H, d, J=9.2 Hz), 5.24 (1H, d, J=3.7 Hz), 4.83 (1H, d, J=7.9 Hz), 4.79 (1H, m), 4.71 (1H, dd, J=7.9, 12.2 Hz), 4.66 (1H, dd, J=3.4, 8.2 Hz), 4.47–4.61 (4H, m), 4.38–4.47 (3H, m), 4.26–4.38 (3H, m), 4.19 (1H, m), 4.14 (2H, m), 3.94 (1H, dd, J=6.4, 10.1 Hz), 2.29 (1H, m), 2.10 (1H, m), 2.02 (1H, m), 1.70–1.90 (4H, m), 1.54 (1H, m), 1.20–1.50 (62H, m), 0.88 (6H, t, J=6.4 Hz).

$^{13}$C (125 MHz, $C_5D_5N$; 27° C.) δ(ppm) 175.2 (s), 105.7 (d), 101.3 (d), 82.6 (d), 77.7 (d), 75.0 (d), 72.8 (d), 72.7 (d), 72.6 (d), 71.9 (d), 70.8 (d), 70.64 (d), 70.55 (d), 68.2 (t), 63.0 (t), 62.5 (t), 52.1 (d), 35.5 (t), 34.0 (t), 32.1 (t), 30.2 (t), 30.03 (t), 30.00 (t), 29.9 (t), 29.62 (t), 29.59 (t) 26.1 (t), 25.9 (t), 22.9 (t), 14.3 (q).

(3) Synthetic Route C

Specific route for preparing the compound having a hydroxyl group at the 4-position of the formula (I) can be shown in the following reaction schemes. The reaction schemes specifically show the preparation of Compounds 1 and 2, and the compounds according to the present invention 3 and 19–30 can also be synthesized in accordance with this process (see FIGS. 3(a)–(b)).

In the schemes shown above, the following abbreviations are used:

Tr: triphenylmethyl,
Bz: benzoyl.

The other abbreviations has the same meanings as those in the schemes shown above.

(i) Synthesis of Compound C1

Compound C1 can be prepared according to the method described in Agricultural and Biological Chemistry, 54 (3), 663–667 (1990).

(ii) Synthesis of Compound C3

To 15.0 g of the Wittig salt (Compound C2) was added 60 ml of tetrahydrofuran, and the reactor was purged with argon. After 14.4 ml of a 2N n-butyl lithium-hexane solution was added at –10° C., the mixture was stirred for 30 minutes. A solution of 5.74 g of the aldehyde (Compound C1) in 10 ml of tetrahydrofuran was added, followed by 8 ml of tetrahydrofuran. The temperature was raised to room temperature, and the mixture was stirred for 15 hours, concentrated, diluted with brine and extracted twice with ethyl acetate. The organic layer was washed with brine, concentrated and purified on a silica gel column (Wako Gel C-200, 200 g, hexane:ethyl acetate=5:1) to give an alcohol (Compound C3) in an amount of 5.06 g (yield 67.6%).

NMR: $^1$H (500 MHz, CDCl$_3$; 27° C.) δ(ppm) 7.20–7.35 (15H, m), 5.71 (1H, m), 5.44 (1H, dd, J=9.5, 10.7 Hz), 5.37 (1H, m), 5.11 (1H, m), 4.30–4.70 (6H, m), 4.42 (1H, dd, J=5.8, 9.5 Hz), 4.06 (1H, m), 3.55 (1H, dd, J=3.0, 5.8 Hz), 3.50 (2H, d, J=6.1 Hz), 2.99 (1H, m), 1.85–2.00 (2H, m), 1.51 (1H, m), 1.1–1.4 (12H, m), 0.85 & 0.84 (each 3H, d, J=6.1 Hz).

(iii) Synthesis of Compound C4

To 0.19 g of the alcohol (Compound C3) were added 1.9 ml of pyridine followed by 50.3 μl of methanesulfonyl chloride at –5° C., and the mixture was stirred at room temperature for 15 hours, concentrated and azeotropically distilled together with toluene. The residue was diluted with diethyl ether and washed with brine, concentrated and purified on a silica gel column (Wako Gel C-200, 10 g, hexane:acetone=6:1) gave an mesyl derivative (Compound C4) in an amount of 0.21 g (yield 97.4%).

MS: FDMS 663.

NMR: $^1$H (500 MHz, CDCl$_3$; 27° C.) δ(ppm) 7.25–7.40 (15H, m), 5.79 (1H, m), 5.48 (1H, t like, J=10.4 Hz), 5.36 (1H, m), 5.00–5.12 (2H, m), 4.75 (1H, d, J=11.6 Hz), 4.35–4.55 (6H, m), 3.76 (1H, m), 3.66 (1H, dd, J=6.7, 10.7 Hz), 3.50 (1H, dd, J=3.0, 10.7 Hz), 2.93 (3H, s), 1.51 (1H, m), 1.10–1.40 (12H, m), 0.85 & 0.84 (each 3H, d, J=6.7 Hz).

(iv) Synthesis of Compound C5

A solution of the mesyl derivative (Compound C4) in 50 ml of ethyl acetate was added 0.58 g of palladium black. The reactor was purged with hydrogen and stirred at room temperature for 15 hours. The catalyst was removed by filtration through celite, and the filtrate was concentrated to give a triol (Compound C5) in an amount of 3.37 g (yield 96.6%).

NMR: $^1$H (500 MHz, CDCl$_3$; 27° C.) δ(ppm) 5.04 (1H, m), 4.04 (2H, m), 3.61 (2H, bs), 3.20 (3H, s), 1.1–1.4 (23H, m), 0.87 (6H, d, J=6.7 Hz).

(v) Synthesis of Compound C6

To 3.37 g of the triol (Compound C5) were added 67.4 ml of dimethylformamide and 4.91 g of sodium azide, and the mixture was stirred at 100° C. for 15 hours and concentrated. Brine was then added to the concentrate, which was extracted with ethyl acetate, washed with brine, concentrated and purified on a silica gel column (Wako Gel C-200, 110 g, hexane:acetone=3:1) to give an azide (Compound C6) in an amount of 2.09 g (yield 71.6%).

$[\alpha]^{24}_D$=+17.7° (CHCl$_3$, c=1.30).

MS: FDMS 344.

IR: (cm$^{-1}$, KBr) 3320, 2910, 2830, 2100, 1460, 1250, 1055.

mp: 63.0°–64.0° C.

NMR: $^1$H (500 MHz, CDCl$_3$; 27° C.) δ(ppm) 3.97 (1H, dd, J=4.9, 11.6 Hz), 3.90 (1H, dt, J=4.3, 11.6 Hz), 3.77 (2H, m), 3.62 (1H, m), 1.52 (1H, m), 1.1–1.4 (22H, m), 0.86 (6H, d, J=6.7 Hz).

$^{13}$C (125 MHz, CDCl$_3$; 27° C.) δ(ppm) 74.6 (d), 72.5 (d), 63.1 (d), 61.7 (t), 39.1 (t), 31.9 (t), 29.9 (t), 29.71 (t), 29.67 (t), 29.60 (t), 29.55 (t), 28.0 (d), 27.4 (t), 25.8 (t), 22.7 (q).

(vi) Synthesis of Compound C7

To 211 mg of the azide (Compound C6) were added 1.1 ml of pyridine and 257 mg of triphenylmethyl chloride, and the mixture was stirred at 50° C. for 15 hours, concentrated, azeotropically distilled with toluene, and purified on a silica gel column (Wako Gel C-200, 15 g, hexane:ethyl acetate= 5:1) to give a trityl derivative (Compound C7) in an amount of 0.30 g (yield 84.0%).

(vii) Synthesis of Compound C8

To 0.30 g of the trityl derivative (Compound C7) was added 3.0 ml of pyridine, followed by 0.18 ml of benzoyl chloride and 5.8 mg of 4-dimethylaminopyridine, and the mixture was stirred. After 15 hours, the mixture with the addition of a small amount of ethanol was concentrated, azeotropically distilled with toluene, and purified on a silica gel column (Wako Gel C-200, 15 g, hexane:ethyl acetate= 12:1) to give a benzoyl derivative (Compound C8) as a syrup in an amount of 0.40 g (yield quantitatively).

MS: FDMS 794.

IR: (cm$^{-1}$, KBr) 2910, 2840, 2090, 1725, 1445, 1250, 1090.

NMR: $^1$H (500 MHz, CDCl$_3$; 27° C.) δ(ppm) 7.88 (2H, bd, J=8.5 Hz), 7.79 (2H, bd, J=8.6 Hz), 7.57 (1H, t, J=7.9 Hz), 7.55 (1H, t, J=7.9 Hz), 7.14–7.47 (19H, m), 5.47 (1H, dt, J=4.3, 7.9 Hz), 5.42 (1H, dd, J=4.3, 6.7 Hz), 3.90 (1H, dt, J=3.1, 7.9 Hz), 3.49 (1H, dd, J=3.1, 9.8 Hz), 3.36 (1H, dd, J=8.2, 10.1 Hz), 1.77 (2H, m), 1.10–1.54 (21H, m), 0.85 (6H, d, J=6.1 Hz).

(viii) Synthesis of Compound C9

To 0.40 g of the benzoyl derivative (Compound C8) were added 8 ml of methylene chloride and 4 ml of methanol, followed by 48.5 mg of p-toluenesulfonic acid monohydrate, and the mixture was stirred at room temperature for 3 days. The reaction mixture was concentrated, diluted with ethyl acetate and aqueous sodium hydrogen carbonate, and the layers were separated. The organic layer was washed with brine, concentrated and purified on a silica gel column (Wako Gel C-200, 10 g, hexane:ethyl acetate=3:1) to give an alcohol (Compound C9) in an amount of 0.22 g (yield 79.7%).

$[\alpha]^{23}_D$=+15.8° (CHCl$_3$, c=1.14).

MS: FDMS 552.

IR: (cm$^{-1}$, KBr) 3360, 2880, 2810, 2080, 1715, 1700, 1595, 1575, 1455, 1445, 1240, 1170, 1100.

mp: 52.5°–54.0° C.

NMR: $^1$H (500 MHz, CDCl$_3$; 27° C.) δ(ppm) 8.02 (2H, d, J=7.3 Hz), 7.98 (2H, d, J=6.7 Hz), 7.60 (1H, t, J=7.3 Hz), 7.55 (1H, t, J=7.6 Hz), 7.46 (2H, t, J=7.6 Hz), 7.41 (2H, t, J=7.9 Hz), 5.51–5.56 (2H, m), 3.98 (1H, m), 3.79 (2H, m), 2.41 (1H, m), 1.85–1.98 (2H, m), 1.51 (1H, m), 1.10–1.5 (20H, m), 0.84 (6H, d, J=6.7 Hz).

(ix) Synthesis of Compound C10

To a solution of 38 mg of the alcohol (Compound C9) in 1 ml of tetrahydrofuran was added 5 mg of palladium black, and the reactor was purged with hydrogen and stirred at room temperature for 15 hours. The reaction mixture was filtered through celite, and the filtrate was concentrated to give an amine (Compound C10), which was directly used in the next reaction.

(x) Synthesis of Compound C11

A solution of 41 mg of p-nitrophenyl α-acetoxytetracosanoate (Compound C11) in 2.0 ml of tetrahydrofuran was added to the amine (Compound C10), and the mixture was stirred at room temperature for 24 hours, concentrated and purified on a silica gel column (Wako Gel C-200, 10 g, hexane:acetone=3:1) to give a ceramide (Compound C12) in an amount of 25.5 mg (yield from Compound C9 39.6%).

Data of Compound C12

MS: FDMS 935.

NMR: $^1$H (500 MHz, CDCl$_3$; 27° C.) δ(ppm) 8.06 & 7.96 (each 2H, d, J=7.3 Hz), 7.64 (1H, t, J=7.3 Hz), 7.54 (1H, t, J=7.6 Hz), 7.50 & 7.39 (each 2H, t, J=7.9 Hz), 7.05 (1H, d, J=9.2 Hz), 5.45 (1H, dd, J=2.4, 9.1 Hz), 5.38 (1H, dt, J=3.1, 9.8 Hz), 5.20 (1H, t, J=6.1 Hz), 4.36 (1H, m), 3.55–3.70 (2H, m), 2.70 (1H, m), 2.03 (2H, m), 1.92 (2H, m), 1.51 (1H, m), 1.1–1.5 (60H, m), 0.89 (3H, t, J=6.7 Hz), 0.86 (6H, d, J=6.7 Hz).

(xi) Synthesis of Compounds C13 and C14

To 130 mg of the ceramide (Compound C12) were added 3.9 ml of tetrahydrofuran, 65.9 mg of stannous chloride, 72.1 mg of silver perchlorate and 400 mg of powdery Molecular Sieves 4A, and the mixture was stirred for 30 minutes. After cooling the mixture to −10° C., a solution of 150.9 mg of benzylglucosyl fluoride (Compound A8) in 1.0 ml of tetrahydrofuran was added. The mixture was raised to room temperature, mixed for 1 hour and filtered through celite. The solids collected were washed with a small amount of acetone. The filtrate and washings were diluted with water, extracted thrice with ethyl acetate, concentrated and purified on a silica gel column (Wako Gel C-200, 10 g, hexane:ethyl acetate=5:1) to give a glucoside (mixture of Compounds C13 and C14) in an amount of 111.6 mg (yield 55.1%).

(xii) Synthesis of Compounds C15 and C16

To 111 mg of the glucoside (mixture of Compounds C13 and C14) were added 3.0 ml of tetrahydrofuran and 30 mg of palladium black, and the mixture was purged with hydrogen and stirred at room temperature for 15 hours. The mixture was filtered through celite, and the filtrate was concentrated to give a tetraol (mixture of Compounds C15 and C16) in an amount of 73.4 mg (yield 87.5%). (xiii) Synthesis of Compounds C19 and C20

To 73.4 mg of the tetraol (mixture of Compounds C15 and C16) were added 4.0 ml of methanol and 0.4 ml of a 1N methanolic sodium methoxide solution, and the mixture was left standing for 2 hours. A resin (DOWEX 50W X8, The Dow Chemical Company) was added to adjust pH to 7 and filtered. The collected solids were sufficiently washed with chloroform-methanol (1:1), and the filtrate and washings were concentrated and purified on a silica gel column (Wako Gel C-200, 7 g, chloroform:methanol=8:1) to give a heptaol (mixture of Compounds C17 and C18) in an amount of 48.5 mg (yield 85.6%).

To 45 mg of the heptaol (mixture of Compounds C17 and C18) were added 2.0 ml of pyridine and 0.3 ml of acetic anhydride, and the mixture was left standing at room temperature for 16 hours. After the addition of a small amount of ethanol, the mixture was stirred, concentrated and purified on a silica gel column (Wako Gel C-200, 8 g, hexane:ethyl acetate=3:1) to isolate the heptaacetate derivatives C19 and C20), respectively in an amount of 35.0 mg (yield 57.7%) and 13.5 mg (yield 22.3%).

Data of Compound C19
MS: FDMS 1040.
NMR: $^1$H (500 MHz, CDCl$_3$; 27° C.) δ(ppm) 7.16 (1H, d, J=9.8 Hz), 5.36 (1H, m), 5.12 (1H, dd, J=5.5, 7.3 Hz), 5.03 (1H, t, J=9.8 Hz), 4.85–4.92 (3H, m), 4.35 (1H, bt, J=9.8 Hz), 4.24 (1H, dd, J=4.6, 12.5 Hz), 4.06 (1H, dd, J=2.1, 12.6 Hz), 3.84 (1H, ddd, J=2.1, 4.6, 10.4 Hz), 3.66 (1H, dd, J=2.7, 10.7 Hz), 3.36 (1H, dd, J=1.2, 10.4 Hz), 2.27, 2.09, 2.08, 2.07, 2.03, 2.01 & 2.00 (each 3H, s), 2.23 (1H, bs), 1.85 (2H, m), 1.62 (2H, m), 1.51 (1H, m), 1.10–1.42 (59H, m), 0.88 (3H, t, J=6.7 Hz), 0.86 (6H, d, J=6.7 Hz).

Data of Compound C20
MS: FDMS 1040.
NMR: $^1$H (500 MHz, CDCl$_3$; 27° C.) δ(ppm) 6.80 (1H, d, J=8.5 Hz), 5.18 (1H, t, J=9.8 Hz), 5.13 (2H, m), 5.06 (1H, t, J=9.5 Hz), 4.89 (1H, dd, J=8.2, 9.5 Hz), 4.87 (1H, m), 4.47 (1H, d, J=8.6 Hz), 4.26 (2H, m), 4.13 (1H, dd, J=2.1, 12.5 Hz), 3.85 (1H, dd, J=2.7, 10.7 Hz), 3.68 (2H, m), 2.23, 2.09, 2.06, 2.02 & 1.99 (each 3H, s), 2.04 (6H, s), 1.83 (2H, m), 1.59 (2H, m), 1.51 (1H, m), 1.10–1.40 (60H, m), 0.88 (3H, t, J=6.7 Hz).

(xiv) Synthesis of Compound C17

To 35.0 mg of the heptaacetate (Compound C19) were added 1.0 ml of methanol and 0.1 ml of a 1N methanolic sodium methoxide solution, and the mixture was left standing for 2.5 hours. A resin (DOWEX 50W X8, The Dow Chemical Company) was added to adjust pH to 7 and filtered. The collected solids were sufficiently washed with chloroform-methanol (1:1), and the filtrate and washings were concentrated and purified on a silica gel column (Wako Gel C-200, 2 g, chloroform:methanol=8:1) to give Compound 1 (C17) in an amount of 22.8 mg (yield 87.8%).

Data of Compound 1
$[\alpha]^{25}_D$=+61.6 (Py, c=1.0).
MS: FDMS 846.
IR: (cm$^{-1}$, KBr) 3320, 2900, 2840, 1635, 1530, 1465, 1360, 1330, 1145, 1020.
mp: 204°–211° C. (broad).
NMR: $^1$H (500 MHz, C$_5$D$_5$N; 27° C.) δ(ppm) 8.45 (1H, d, J=9.2 Hz), 6.77 (1H, d, J=6.7 Hz), 6.32 (1H, m), 6.08 (1H, d, J=6.1 Hz), 5.63 (1H, d, J=3.7 Hz), 5.30 (1H, m), 4.65 (1H, m), 4.58 (1H, m), 4.10–4.48 (9H, m), 2.29 (1H, m), 2.20 (1H, m), 2.01 (1H, m), 1.10–2.05 (63H, m), 0.88 (3H, t, J=6.7 Hz), 0.87 (6H, d, J=6.7 Hz).
$^{13}$C (125 MHz, C$_5$D$_5$N; 27° C.) δ(ppm) 175.0 (s), 100.8 (d), 76.6 (d), 75.4 (d), 74.7 (d), 73.4 (d), 72.4 (d), 72.2 (d), 71.8 (d), 67.7 (t), 62.7 (t), 50.2 (d), 39.3 (t), 35.6 (t), 34.6 (t), 32.1 (t), 30.4 (t), 30.3 (t), 30.2 (t), 30.0 (t), 29.9 (t), 29.6 (d), 28.2 (t), 27.7 (t), 26.4 (t), 25.9 (t), 22.9 (t), 22.8 (t), 14.3 (q).

(xv) Synthesis of Compound C18

To 13.5 mg of the heptaacetate (Compound C20) were added 1.0 ml of methanol and 0.1 ml of a 1N methanolic sodium methoxide solution, and the mixture was left standing for 2 hours. A resin (DOWEX 50W X8, The Dow Chemical Company) was added to adjust pH to 7 and filtered. The collected solids were sufficiently washed with chloroform-methanol (1:1), and the filtrate and washings were concentrated and purified on a silica gel column (Wako Gel C-200, 1.5 g, chloroform:methanol=8:1) to give Compound 2 (C18) in an amount of 8.6 mg (yield 86.0%).

Data of Compound 2
$[\alpha]^{25}_D$=−3.1° (Py, c=0.39).
MS: FDMS 846.
IR: (cm$^{-1}$, KBr) 3330, 2900, 2830, 1625, 1530, 1460, 1375, 1360, 1070.
mp: 223°–226° C.
NMR: $^1$H (500 MHz, C$_5$D$_5$N; 27° C.) δ(ppm) 8.57 (1H, d, J=9.2 Hz), 6.81 (1H, m), 6.00 (1H, m), 5.29 (2H, m), 4.97 (1H, d, J=7.9 Hz), 4.72 (1H, m), 4.48–4.61 (4H, m), 4.30–4.38 (2H, m), 4.15–4.25 (3H, m), 4.02 (1H, m), 3.88 (1H, m), 2.15–2.30 (2H, m), 2.02 (1H, m), 1.85–1.95 (2H, m), 1.60–1.85 (3H, m), 1.50 (1H, m), 1.10–1.45 (56H, m), 0.878 (6H, d, J=6.7 Hz), 0.876 (3H, t, J=6.7 Hz).
$^{13}$C (125 MHz, C$_5$D$_5$N; 27 °C.) δ(ppm) 175.6 (s), 105.6 (d), 78.5 (d), 78.4 (d), 75.8 (d), 75.1 (d), 72.5 (d), 72.4 (d), 71.5 (d), 70.5 (t), 62.6 (t), 51.8 (d), 39.3 (t), 35.6 (t), 34.1 (t), 32.1 (t), 30.4 (t), 30.3 (t), 30.2 (t), 30.0 (t), 29.9 (t), 29.6 (d), 28.2 (t), 27.7 (t), 26.6 (t), 25.9 (t), 22.9 (t), 22.8 (t), 14.3 (q).

In the synthesis of Compound 1 in Route C, benzylgalactosyl trichloroacetimidate and a boron trifluoride-ether complex in place of benzylglucosyl fluoride (Compound A8) were reacted with the ceramide C12 to form a β-bond, and the synthesis was continued in accordance with Route C to give Compound 3.

Data of Compound 3
$[\alpha]^{25}_D$=+4.9° (Py, c=0.97).
MS: FDMS 848.
IR: (cm$^{-1}$, KBr) 3340, 2910, 2840, 1635, 1625, 1530, 1465, 1070.
mp: 204°–211° C. (broad).
NMR: $^1$H (500 MHz, C$_5$D$_5$N; 27° C.) δ(ppm) 8.54 (1H, d, J=8.5 Hz), 5.27 (1H, m), 4.88 (1H, d, J=7.9 Hz), 4.76 (1H, dd, J=6.4, 10.7 Hz), 4.38–4.58 (7H, m), 4.28 (1H, m), 4.19 (1H, m), 4.11 (1H, dd, J=3.1, 9.2 Hz), 2.21 (2H, m), 1.99 (1H, m), 1.91 (2H, m), 1.78 (1H, m), 1.69 (2H, m), 1.50 (1H, m), 1.10–1.42 (56H, m), 0.88 (6H, d, J=6.7 Hz), 0.87 (3H, t, J=6.7 Hz).

(4) Synthetic Route D

The compound having a hydroxyl group at the 4-position of the long chain base can also be prepared according to the following reaction schemes in the same manner as in Synthetic Route C. The reaction schemes show the preparation of Compound 19, and the compounds according to the present invention 1, 2, 3 and 20–30 can also be synthesized in accordance with this process (see FIGS. 4(a)–(c)).

Abbreviations in the figures have the same meanings as those in the schemes shown above.

(i) Synthesis of Compound D2

To a suspension of 20 g (0.133 mol) of D-lyxose (Compound D1) in 300 ml of acetone dehydrated with calcium chloride was added 0.05 ml of concentrated sulfuric acid, and the mixture was stirred at room temperature for 18 hours. Molecular Sieves 4A (10.0 g) was added for neutralization. The mixture was filtered, and the residue was washed sufficiently with acetone. The washings and the filtrate were combined, concentrated under reduced pressure, and used for the next reaction without purification.

(ii) Synthesis of Compound D3

To a solution of the total amount of Compound D2 obtained in the previous reaction in 168 ml of methylene chloride were added 10.0 ml of pyridine and 39.0 g of trityl chloride, and the mixture was stirred at 32° C. for 4 hours. After 7.8 ml of ethanol was added, the mixture was stirred and washed with an saturated aqueous ammonium chloride solution, followed by a saturated aqueous sodium hydrogen carbonate solution and saturated brine. To a syrup obtained by concentration under reduced pressure was added 20 ml of ethyl acetate. Hexane (40 ml) was added slowly to this solution, and when the mixture became turbid, it was left standing with a crystal seed at 0° C. Crystals thus obtained were filtered and washed with a mixed solvent of hexane/ethyl acetate=8/1. The primary crystal was obtained in an amount of 44.4 g, and the secondary crystal was obtained from the mother liquor in an amount of 5.6 g (yield 86.8%).
m.p. 174°–176° C.;

FD-MS=432 ($C_{27}H_{28}O_5$; MW=432.19);
IR (cm$^{-1}$, KBr) 3530, 3400, 3050, 2950, 2880, 1600, 1490, 1450, 1375, 1215, 1070;
$^1$H-NMR (500 MHz/CDCl$_3$) δ(ppm) 7.48 (6H, d, J=7.3 Hz), 7.29 (6H, t, J=7.3 Hz), 7.22 (3H, t, J=7.3 Hz), 5.38 (1H, d, J=2.4 Hz), 4.75 (1H, dd, J=5.5, 3.7 Hz), 4.59 (1H, d, J=6.1 Hz), 4.32–4.34 (1H, m), 3.43 (1H, dd, J=4.9, 9.8 Hz), 3.39 (1H, dd, 6.7, 9.8 Hz), 2.33 (1H, d, J=2.4 Hz), 1.29 (3H, s), 1.28 (3H, s).

(iii) Synthesis of Compound D4

To 96.4 g of 1-bromotridecane was added 96.0 g of triphenylphosphine, and the mixture was stirred at 140° C. for 4.5 hours, and then cooled gradually. Tetrahydrofuran (500 ml) was added to dissolve the mixture, which was then cooled to 0° C. A 2.5N n-butyl lithium solution (146.4 ml) was added dripwise, and the mixture was stirred for 15 minutes. A solution of Compound D3 (79 g) in tetrahydrofuran (150 ml) was added to the mixture. The mixture was stirred for 18 hours, while the temperature was gradually raised to room temperature. After the mixture was concentrated under reduced pressure, 1000 ml of a mixture of hexane/methanol/water=10:7:3 was added to the concentrate, followed by 40 ml of a saturated aqueous ammonium chloride solution. The layers were separated.

The methanol/water layer was extracted again with 500 ml of hexane. The total hexane layer thus obtained was dried over anhydrous magnesium sulfate, concentrated under reduced pressure and further dried sufficiently under reduced pressure with a vacuum pump to give a crude product of Compound D4 as a syrup, which was used for the next reaction without further purification.

(iv) Synthesis of Compound D5

To the total amount of Compound D4 obtained in the previous reaction were added 600 ml of methylene chloride, 200 ml of pyridine and 16.95 ml of methanesulfonyl chloride, and the mixture was stirred at 31° C. for 24 hours. Ethanol (13 ml) was added to the mixture, which was stirred at room temperature for 1 hour and concentrated under reduced pressure. 1,000 ml of the mixture of hexane/methanol/water=10/7/3 was added to the concentrate, and the layers were separated. The methanol/water layer was re-extracted thrice with 200 ml of hexane. The total hexane layer was dried over anhydrous magnesium sulfate, concentrated under reduced pressure and further dried sufficiently under reduced pressure with a vacuum pump to give a crude product of Compound D5 as a syrup, which was used for the next reaction without further purification.

(v) Synthesis of Compound D6

To the total amount of Compound D5 obtained in the previous step were added 900 ml of methylene chloride and 600 ml of methanol. To this solution was added 124 ml of concentrated hydrochloric acid, and the mixture was stirred at room temperature for 5 hours. Sodium hydrogen carbonate was added for neutralization, and the mixture was filtered. The residue was washed with ethyl acetate. The ethyl acetate washings were combined with the filtrate and concentrated under reduced pressure. Ethyl acetate was added to the residue, and the mixture was washed with saturated brine. The aqueous layer was re-extracted thrice with ethyl acetate, and the total ethyl acetate layer thus obtained was dried over anhydrous magnesium sulfate and concentrated under reduced pressure. Crystallization from hexane gave the primary crystal in an amount of 41.0 g and the secondary crystal in an amount of 9.40 g. Overall yield throughout these three steps was 70.0%.

mp: 66°–67° C.;
FD-MS=377(M-H$_2$O)$^+$, ($C_{19}H_{38}O_6S$, MW=394.57);
IR: (cm$^{-1}$, KBr) 3500, 3350, 2920, 2850, 1465, 1440, 1355, 1330, 1160, 1030, 930.
$^1$H-NMR (500 MHz/CDCl$_3$+D$_2$O-1 drop); E/Z mixture (3:7) 5.86 (0.3H, dt, J=7.3, 14.7 Hz), 5.77 (0.7 H, dt, J=7.3, 10.4 Hz), 5.55 (0.3H, br. dd, J=7.3, 14.7 Hz), 5.49 (0.7H, br. t, J=9.8 Hz), 4.91–4.97 (1H, m), 4.51 (0.7H, br. t, J=9.8 Hz), 4.11 (0.3H, br. t, J=7.3 Hz), 3.94–4.03 (2H, m), 3.67–3.73 [1H (3.70, dd, J=3.1, 6.7 Hz), (3.69, dd, J=3.1, 7.3 Hz)], 3.20 (2.1H, s), 3.19 (0.9H, s), 2.05–2.22 (2H, m), 1.22–1.43 (20H, m), 0.88 (3H, t, J=6.7 Hz).

(vi) Synthesis of Compound D7

To a solution of 24.4 g of Compound D6 in 244 ml of tetrahydrofuran was added 2.44 g of 5% palladium-barium sulfate. The reactor was purged with hydrogen gas, and the mixture was stirred under hydrogen atmosphere at room temperature for 20 hours. After diluted with 200 ml of a mixed solvent of chloroform/methanol=1:1 at 60° C., the mixture was filtered through celite and the residue was washed with the mixed solvent of chloroform/methanol=1:1. The filtrate and the washings were combined and concentrated under reduced pressure, the concentrate was crystallized from ethyl acetate, and crystals were washed well with hexane to give 21.5 g of the primary crystals and 0.64 g of the secondary crystals in a yield of 91.3%.

mp: 124°–126° C.;
FD-MS=397($C_{19}H_{40}O_6S$, Mw=396.59);
[α]$^{23}_D$=+7.52° (c=1.50, $C_5H_5N$);
IR (cm$^{-1}$, KBr) 3500, 3380, 3220, 2920, 2850, 1470, 1430, 1360, 1330, 1165, 1095, 930;
$^1$H-NMR (500 MHz/CDCl$_3$—CD$_3$OD=1:1) 4.93–4.96 (1H, m), 3.91 (1H, dd, J=6.7, 12.2 Hz), 3.85 (1H, dd, J=4.9, 12.2 Hz), 3.54–3.60 (1H, m), 3.50 (1H, dd, J=1.8, 8.5 Hz), 3.19 (3H, s), 1.75–1.83 (1H, m), 1.53–1.62 (1H, m), 1.21–1.45 (24H, m), 0.89 (3H, t, J=6.7 Hz).

(vii) Synthesis of Compound D8

To a solution of 8.94 g (22.5 mmol) of Compound D7 in 72 ml of dry DMF was added 2.93 g of NaN$_3$. The mixture was heated to 95° C. in an oil bath and stirred for 4 hours. After the raw material was confirmed to disappear by TLC (hexane:acetone=3:2), the reaction mixture was concentrated under reduced pressure. The residual concentrate diluted with ethyl acetate was washed with water, and the aqueous layer was re-extracted with the equal volume of ethyl acetate. The combined ethyl acetate layers were washed with brine, dried over anhydrous magnesium sulfate, concentrated under reduced pressure and desiccated well by a vacuum pump. The product was directly used for the next reaction without purification.

(viii) Synthesis of Compound D9

To the total amount of powder obtained in the previous step was added 45 ml of dichloromethane, followed by 7.53 g of TrCl and 14 ml of pyridine, sequentially, and the mixture was stirred at room temperature for 16 hours. After the raw material was confirmed to disappear by TLC (hexane:ethyl acetate=2:1), the reaction was quenched with 1.8 ml of ethanol and further stirred for 30 minutes. The reaction mixture was washed with a saturated aqueous sodium hydrogen carbonate solution, a saturated ammonium chloride solution and saturated brine, dried over anhydrous magnesium sulfate, and concentrated under reduced pressure. The syrup thus obtained was purified on a silica gel column (hexane:ethyl acetate=10:1) to give D9 in an amount of 6.93 g (yield 52%).

FD-MS=585($C_{37}H_{51}N_3O_3$; Mw=585.82);
[α]$^{23}_D$=+11.86° (c=0.86, CHCl$_3$);
IR (cm$^{-1}$, film) 3425, 2924, 2854, 2098, 1491, 1466, 1448, 1267, 1223, 1074, 1034;

¹H-NMR (500 MHz/CDCl₃+D₂O-1 drop) 7.24–7.61 (15H, m), 3.62–3.66 (2H, m), 3.51–3.57 (2H, m), 3.42 (1H, dd, J=6.0, 10.4 Hz), 1.23–1.56 (26H, m), 0.88 (3H, t, J=6.7 Hz).

(ix) Synthesis of Compound D10

To a solution of 21.73 g of Compound D9 in the form of syrup in 200 ml of dimethylformamide was added portionwise 3.57 g of 60% sodium hydride. After the mixture was stirred at room temperature for 40 minutes, 9.71 ml (1.05 equivalent) of benzyl bromide was added dropwise under ice-cooling, and the mixture was stirred for 2.5 hours with the temperature raising up to room temperature. After the raw material was confirmed to disappear by TLC (hexane:ethyl acetate=10:1), the reaction was quenched with cracked ice. The reaction mixture was diluted with 50 ml of water and extracted thrice with ethyl acetate. The ethyl acetate layer was washed thrice with saturated brine, dried over anhydrous magnesium sulfate, and concentrated under reduced pressure. The syrup thus obtained was purified on a silica gel column (hexane:ethyl acetate=100:1) to give D10 in an amount of 23.97 g (yield 84.4%).

FD-MS=738(M−N₂)⁺ (C₅₁H₆₃N₃O₃; Mw=766.07);
$[\alpha]^{23}_D$=+9.75° (c=0.97, CHCl₃);
IR (cm⁻¹, film) 3062, 3031, 2925, 2854, 2096, 1492, 1465, 1450;
¹H-NMR (500 MHz, CDCl₃) 7.07–7.48 (25H, m), 4.57 (1H, d, J=11.0 Hz), 4.44 (1H, d, J=11.0 Hz), 4.41 (2H, s), 3.73–3.79 (1H, m), 3.46–3.56 (2H, m), 3.37 (1H, dd, J=8.6, 10.4 Hz), 1.20–1.64 (26H, m), 0.88 (3H, t, J=6.7 Hz).

(x) Synthesis of Compound D11

To a solution of 25.35 g (33.14 mmol) of the raw material D10 in 200 ml of 1-propanol and 25 ml of methanol were added 16.72 g of ammonium formate and 1.0 g of 10% palladium on carbon, and the mixture was stirred at room temperature for 16 hours. After confirming the disappearance of the raw material and the production of the aimed product by TLC (hexane:acetone=3:1), the reaction was diluted with 50 ml of ethyl acetate and filtered through celite. After washed with ethyl acetate, the mixture was concentrated under reduced pressure. The residual concentrate was diluted with ethyl acetate and washed twice with a saturated aqueous NaHCO₃ solution. The aqueous layer was re-extracted with ethyl acetate, and the combined ethyl acetate layer was washed with saturated brine, dried over anhydrous magnesium sulfate, concentrated under reduced pressure, and azeotropically distilled with toluene. The product was next desiccated sufficiently by a vacuum pump and used for the next step without purification.

(xi) Synthesis of Compound D12

To a solution of the total amount of Compound D11 in the form of syrup obtained in the previous step in 250 ml of methylene chloride were added 12.49 g of cerotic acid and 7.13 g of WSC hydrochloride. The mixture was heated and refluxed at 50° C. for 2 hours in an oil bath. As the raw material still remained in the reaction mixture by TLC (hexane:acetone=3:1), the mixture was further heated under reflux with addition of 620 mg of cerotic acid and 360 mg of WSC hydrochloride for 1 hour. Cooled to room temperature, the reaction mixture was sequentially washed with a 0.5N aqueous hydrochloric acid solution, saturated brine, a saturated aqueous sodium hydrogen carbonate solution, and saturated brine. The mixture was dried over anhydrous magnesium sulfate, concentrated under reduced pressure, desiccated well by a vacuum pump, and used for the next reaction without purification.

(xii) Synthesis of Compound D13

To a solution of the total amount of Compound D12 in the form of syrup obtained in the previous step in 120 ml of methylene chloride and 30 ml of methanol were added dropwise 3 ml of a 10% hydrochloric acid-methanol solution, and the mixture was stirred at room temperature for 2 hours. After having confirmed the completion of the reaction by TLC (hexane:acetone=3:1), the mixture was neutralized with sodium hydrogen carbonate. The mixture was filtered through celite, washed twice with saturated brine, dried over anhydrous magnesium sulfate, and concentrated under reduced pressure. The concentrate was azeotropically distilled with toluene. The residue was dissolved in acetone under heating and stored at 0° C. to give white precipitates in an amount of 22.2 g (overall yield throughout three steps 76.6%).

mp=75°–76.5° C.;
FD-MS=876(C₅₈H₁₀₁NO₄, Mw=876.43);
$[\alpha]^{23}_D$=−29.7° (c=0.675, CHCl₃);
IR (cm⁻¹, KBr) 3334, 2918, 2850, 1637, 1618, 1548, 1469, 1103, 1052;
¹H-NMR (500 MHz, CDCl₃) 7.30–7.47 (10H, m, Ph), 6.07 (1H, d, J=7.9 Hz), 4.72 (1H, d, J=11.6 Hz), 4.66 (1H, d, J=11.6 Hz), 4.61 (2H, d, J=11.6 Hz), 4.24–4.32 (1H, m), 4.45 (1H, d, J=11.6 Hz), 4.00 (1H, dt, $J_t$=7.3 Hz, $J_d$=4.3 Hz), 3.67–3.72 (2H, m), 3.61 (1H, ddd, J=4.3, 11.6, 8.6 Hz), 3.05 (1H, dd, J=4.3, 8.5 Hz), 1.94–2.05 (2H, m), 1.15–1.69 (72H, m), 0.88 (6H, t, J=6.1 Hz).

(xiii) Synthesis of Compound D14

1) To a solution of 454 mg of the glucose derivative (Compound E1) in 3.0 ml of methylene chloride was added 0.82 ml of trimethylsilyl bromide, and the mixture was stirred at room temperature for 5 hours. The reaction mixture was directly concentrated under reduced pressure and desiccated in vacuum, and the residue was used for the next reaction.

2) To a solution of 340 mg of Compound D13 in 2.5 ml of methylene chloride and 2.5 ml of dimethylformamide was added 500 mg of activated Molecular Sieves 4A, followed by 240 mg of tetraethylammonium bromide, and the mixture was stirred. The solution of the glucose derivative (Compound E2) obtained in the previous step (1) in 2.5 ml of methylene chloride was added to the mixture, and the total mixture was stirred at room temperature for 18 hours. The reaction mixture diluted with 5 ml of methylene chloride was filtered through celite. The residue was washed well with methylene chloride. The combined organic layer was washed with a saturated aqueous sodium hydrogen carbonate solution and saturated brine in sequence, dried over anhydrous magnesium sulfate, concentrated under reduced pressure, and purified on a silica gel column (hexane:ethyl acetate=10:1–8:1) to give the product in an amount of 330 mg (yield 60.8%).

FD-MS=1399(C₉₂H₁₃₅NO₉, Mw=1399.07);
¹H-NMR (500 MHz, CDCl₃) 7.22–7.33 (28H, m), 7.12–7.14 (2H, m), 5.91 (1H, d, J=8.5 Hz), 4.95 (1H, d, J=11.0 Hz), 4.77–4.83 (5H, m), 4.70 (1H, d, J=11.6 Hz), 4.42–4.62 (6H, m), 4.17–4.24 (1H, m), 3.90–3.95 (2H, m), 3.87 (1H, dd, J=3.0, 6.7 Hz), 3.79 (1H, dd, J=3.7, 10.4 Hz), 3.72–3.76 (1H, m), 3.52–3.68 (5H, m), 1.91–1.99 (2H, m), 1.21–1.70 (72H, m), 0.88 (6H, t, J=6.7 Hz).

(xiv) Synthesis of Compound D19

To a solution 300 mg of Compound D14 in 6 ml of tetrahydrofuran was added 50 mg of 5% palladium-barium sulfate. The reactor was purged with hydrogen gas, and the mixture was stirred under hydrogen atmosphere at room temperature for 16 hours. The reaction mixture was filtered through celite and washed with a mixed solvent of chloroform/methanol=2:1. The combined organic layer was concentrated under reduced pressure, and white powder thus obtained was purified on a silica gel column (chloroform:methanol=10:1–7:1) to give Compound 19 in an amount of 165 mg (yield 90.0%).

mp=152°–155° C.; negative FAB-MS/triethanolamine:856 (M–H)⁻;

$[\alpha]^{23}_D$=+43.9° (c=0.81, $C_5H_5N$);

IR (cm$^{-1}$, KBr) 3380, 2920, 2850, 1632, 1552, 1468, 1130, 1076;

$^1$H-NMR (500 MHz, $C_5D_5N$) 8.34 (1H, d, J=8.5 Hz), 7.31 (1H, bs), 7.10 (1H, bs), 7.04 (1H, bs), 6.47 (1H, d, J=5.5 Hz), 6.32 (1H, m), 6.04 (1H, bs), 5.57 (1H, d, J=3.7 Hz), 5.21–5.28 (1H, m), 4.66 (1H, dd, J=5.5, 11.0 Hz), 4.54 (1H, bt, J=9.2 Hz), 4.26–4.45 (6H, m), 4.08–4.22 (2H, m), 2.40 (2H, t, J=7.3 Hz), 2.22–2.30 (1H, m), 1.77–1.94 (4H, m), 1.59–1.68 (1H, m), 1.24–1.47 (66H, m), 0.88 (6H, t, J=6.7 Hz);

$^{13}$C-NMR (125 MHz, $C_5D_5N$) 173.2 (s), 101.0 (d), 76.7 (d), 75.4 (d), 74.6 (d), 73.5 (d), 72.3 (d), 71.9 (d), 68.1 (t), 62.7 (t), 51.3 (d), 36.8 (t), 34.4 (t), 32.1 (t), 30.4 (t), 30.1 (t), 30.05 (t), 30.02 (t), 29.93 (t), 29.88 (t), 29.82 (t), 29.76 (t), 29.6 (t), 26.5 (t), 26.4 (t), 23.0 (t), 14.3 (q).

Synthesis of Compound 20

In the synthesis of Compound 19 in Route D, Compound 20 was prepared in the same manner as in Route D, except that the Wittig reagent which is reacted with Compound D3 is prepared from triphenylphosphine and 1-bromooctane in place of triphenylphosphine and 1-bromotridecane, and that lignoceric acid in place of cerotic acid is reacted with Compound D11.

Synthesis of Compound 21

In the synthesis of Compound 19 in Route D, Compound 21 was prepared in the same manner as in Route D, except that the Wittig reagent which is reacted with Compound D3 is prepared from triphenylphosphine and 1-bromohexadecane in place of triphenylphosphine and 1-bromotridecane, and that lignoceric acid in place of cerotic acid is reacted with Compound D11.

Synthesis of Compound 22

In the synthesis of Compound 19 in Route D, Compound 22 was prepared in the same manner as in Route D, except that the Wittig reagent which is reacted with Compound D3 is prepared from triphenylphosphine and 1-bromohexane in place of triphenylphosphine and 1-bromotridecane, and that acetic acid in place of cerotic acid is reacted with Compound D11.

Synthesis of Compound 23

In the synthesis of Compound 19 in Route D, Compound 23 was prepared in the same manner as in Route D, except that the Wittig reagent which is reacted with Compound D3 is prepared from triphenylphosphine and 1-bromodecane in place of triphenylphosphine and 1-bromotridecane, and that myristic acid in place of cerotic acid is reacted with Compound D11.

Synthesis of Compound 24

In the synthesis of Compound 19 in Route D, Compound 24 was prepared in the same manner as in Route D, except that the Wittig reagent which is reacted with Compound D3 is prepared from triphenylphosphine and 1-bromotetradecane in place of triphenyl-phosphine and 1-bromotridecane, and that capric acid in place of cerotic acid is reacted with Compound D11.

Synthesis of Compound 25

In the synthesis of Compound 19 in Route D, Compound 25 was prepared in the same manner as in Route D, except that the Wittig reagent which is reacted with Compound D3 is prepared from triphenylphosphine and 1-bromododecane in place of triphenylphosphine and 1-bromotridecane, and that arachidic acid in place of cerotic acid is reacted with Compound D11.

Synthesis of Compound 26

In the synthesis of Compound 19 in Route D, Compound 26 was prepared in the same manner as in Route D, except that the Wittig reagent which is reacted with Compound D3 is prepared from triphenylphosphine and 1-bromohexadecane in place of triphenyl-phosphine and 1-bromotridecane, and that 2-(R)-hydroxycerotic acid in place of cerotic acid is reacted with Compound D11.

Synthesis of Compound 27

In the synthesis of Compound 19 in Route D, Compound 27 was prepared in the same manner as in Route D, except that the Wittig reagent which is reacted with Compound D3 is prepared from triphenylphosphine and 1-bromododecane in place of triphenylphosphine and 1-bromotridecane, and that 2-(R)-hydroxystearic acid in place of cerotic acid is reacted with Compound D11.

Synthesis of Compound 28

In the synthesis of Compound 19 in Route D, Compound 28 was prepared in the same manner as in Route D, except that the Wittig reagent which is reacted with Compound D3 is prepared from triphenylphosphine and 1-bromooctane in place of triphenylphosphine and 1-bromotridecane, and that 2-(R)-hydroxycaprylic acid in place of cerotic acid is reacted with Compound D11.

Synthesis of Compound 29

In the synthesis of Compound 19 in Route D, Compound 29 was prepared in the same manner as in Route D, except that the Wittig reagent which is reacted with Compound D3 is prepared from triphenylphosphine and 1-bromotetradecane in place of triphenyl-phosphine and 1-bromotridecane, and that 2-(R)-hydroxylignoceric acid in place of cerotic acid is reacted with Compound D11.

Synthesis of Compound 30

In the synthesis of Compound 19 in Route D, Compound 30 was prepared in the same manner as in Route D, except that the Wittig reagent which is reacted with Compound D3 is prepared from triphenylphosphine and 1-bromotetradecane in place of triphenyl-phosphine and 1-bromotridecane, and that 2-(S)-hydroxylignoceric acid in place of cerotic acid is reacted with Compound D11.

EXPERIMENTAL EXAMPLE 1

Anti-tumor activity of the compound according to the present invention

Anti-tumor activity against B16 mouse melanoma cells inoculated subcutaneously

Experiment was performed with groups consisting of 6 female BDF$_1$ mice, 6 weeks old, purchased from NIPPON SLC K.K. B16 mouse melanoma cells (1×10⁶) were inoculated subcutaneously in the rear part of mice (0 day). On 1, 5 and 9 days after inoculation, a sample in a level of 0.1 mg/kg was administered to the tail vein in a dose of 0.2 ml/20 g/ mouse. The volume of tumor in the subcutaneous rear part [(long diameter×short diameter×height)/2] was measured on 8, 12, 16 and 20 days to determine the tumor growth inhibiting rate (TGIR) of each sample. These results were compared with those obtained with control samples. The TGIR after 20 days are shown in Table 1.

In this connection, respective test runs were separated with bloken lines in Table 1.

TABLE 1

Tumor growth inhibiting effect against B16 mouse melanoma cells

| Sample | TGIR (%) |
|---|---|
| 1 | 66.2 |
| 2 | 35.9 |
| 3 | 51.9 |
| 4 | 42.3 |
| 5 | 61.5 |
| 6 | 10.1 |
| 8 | 4.2 |
| 9 | 28.3 |
| 11 | 28.4 |
| 12 | 57.5 |
| 13 | 27.2 |
| 14 | 58.1 |
| 15 | 50.6 |
| 16 | 21.6 |
| 17 | 43.0 |
| 18 | 22.5 |
| 19 | 53.0 |

All of the compounds used for the test exhibited the inhibition of tumor growth.

EXPERIMENTAL EXAMPLE 2

Immunostimulating activities of the compounds of the present invention

Mixed lymphocyte culture reaction

C57BL/6 mouse spleen cells treated with 50 μg/ml of Mitomycin C for 30 minutes were used as the target cells, and BALB/c mouse spleen cells were used as the reactant cells. These spleen cells were cultured in a level of 2×10$^6$ cells/ml, respectively, in 10% FCS RPMI 1640 as a medium. Both cells in a level of 50 μl/well and a sample (10 μl/well) were added to a round bottomed 96-well plate and cultured at 37° C. under the atmosphere of 5% $CO_2$ for 42 hours. $^3$H-thymidine ($^3$H-TdR) was added in a level of 0.5 μCi/well. The cells were harvested after 8 hours, and the level of the incorporated $^3$H-TdR was determined by a liquid scintillation counter.

As shown in Table 2, all of the samples exhibited lymphocyte mixed culture reaction stimulating activities.

TABLE 2

Incorporation of $^3$H-TdR (% based on the control)

| Sample | 10$^0$ (μg/ml) |
|---|---|
| 1 | 182 |
| 2 | 159 |
| 3 | 127 |
| 4 | 203 |
| 5 | 199 |
| 6 | 134 |
| 7 | 138 |
| 8 | 220 |
| 9 | 114 |
| 10 | 210 |
| 11 | 259 |
| 12 | 517 |
| 13 | 246 |
| 14 | 150 |
| 15 | 143 |
| 16 | 130 |
| 17 | 374 |
| 18 | 137 |
| 19 | 177 |

INDUSTRIAL APPLICABILITY

The compound of the present invention is a sphingoglycolipid having an excellent anti-tumor activity and immunostimulating activity and exhibiting the effects at a small dose with few side-effects, and is useful as an anti-tumor agent and an immunostimulating agent.

What is claimed is:

1. A sphingoglycolipid represented by formula (I):

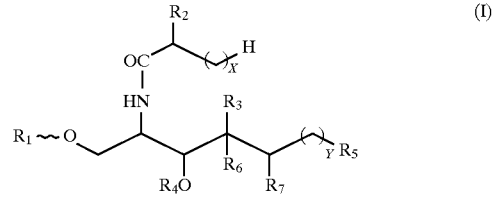

wherein X denotes an integer from 10 to 24, Y denotes an integer from 9 to 13;

$R_1$ represents α-6-deoxygalactopyranosyl, α-galactopyranosyl, α-glucopyranosyl, α-6-deoxygalactofuranosyl, β-6-deoxygalactofuranosyl or β-arabinopyranosyl;

$R_2$ represents H or OH;

$R_3$ represents H or OH;

$R_4$ represents a galactosyl group or H;

$R_5$ represents a methyl or isopropyl group;

$R_6$ and $R_7$, each independently represent H;

provided that when $R_1$ represents α-glucopyranosyl, $R_3$ represents OH; and when $R_1$ represents α-galactopyranosyl, $R_2$ represents OH and $R_4$ represents galactosyl.

2. A sphingoglycolipid according to claim 1 which is selected from the group of compounds consisting of:

(1) (2S,3S,4R)-1-(α-D-glucopyranosyloxy)-2-[(R)-2-hydroxytetracosanoylamino]-16-methyl-3,4-heptadecanediol, (2) (2S,3R)-1,3-di(α-D-galactopyranosyloxy)-2-[(R)-2-hydroxytetracosanoylamino]octadecane, (3) (2S,3R)-1-(α-D-galactopyranosyloxy)-3-(β-D-galactopyranosyloxy)-2-[(R)-2-hydroxytetracosanoylamino]octadecane, (4) (2S,3R)-1-(6'-deoxy-α-D-galactopyranosyloxy)-2-tetradecanoylamino-3-octadecanol, (5) (2S,3R)-1-(6'-deoxy-α-D-galactofuranosyloxy)-2-tetradecanoylamino-3-octadecanol, (6) (2S,3R)-1-(6'-deoxy-β-D-galactofuranosyloxy)-2-tetradecanoylamino-3-octadecanol, (7) (2S,3R)-1-(β-L-arabinopyranosyloxy)-2-tetradecanoylamino-3-octadecanol, and (8) (2S,3S,4R)-1-(α-D-glucopyranosyloxy)-2-hexacosanoylamino-3,4-octadecanediol.

3. A process for preparing the compound represented by formula (I) according to claim 1 which comprises reacting an aldehyde compound represented by formula (VI)

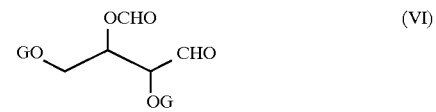

with an alkane compound having from 9–13 carbon atoms to obtain an alcohol compound represented by formula (VII)

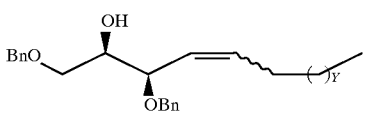

(VII)

converting the hydroxy group to a leaving group, converting the leaving group to an azide group, reducing the azidation product into an amine compound represented by formula (VIII)

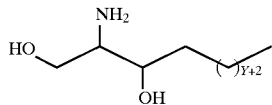

(VIII)

reacting the amine compound of formula (VIII) with an active carboxylate having 9–13 carbon atoms to form an amide derivative, reacting the amide derivative with a compound selected from the group of monosaccharides consisting of hexosyl, pentosyl and deoxyhexosyl derivatives to form a protected product and deprotecting the protected product to form a glycosyl derivative.

4. A pharmaceutical composition comprising a compound according to claim 1 as an active ingredient and a pharmaceutically acceptable carrier or diluent.

5. A process for inhibiting the growth of a tumor, wherein a compound according to claim 1 is administered to a patient in need of inhibition of the growth of the tumor.

6. A process for stimulating the immune system of a patient in need thereof comprising administering a compound according to claim 1 to the patient.

* * * * *